United States Patent
Rittman, III et al.

(10) Patent No.: US 10,350,108 B1
(45) Date of Patent: Jul. 16, 2019

(54) HEATING/COOLING THERAPY SYSTEM

(71) Applicant: W&M Tech Advisors, LLC, Wellington, FL (US)

(72) Inventors: William J. Rittman, III, Wellington, FL (US); Marsha Calise, Wellington, FL (US); Steven Woolfson, Boston, MA (US)

(73) Assignee: W&M Tech Advisors, LLC, Wellington, FL (US)

( * ) Notice: Subject to any disclaimer, the term of this patent is extended or adjusted under 35 U.S.C. 154(b) by 0 days.

(21) Appl. No.: 16/116,316

(22) Filed: Aug. 29, 2018

Related U.S. Application Data

(60) Provisional application No. 62/694,281, filed on Jul. 5, 2018.

(51) Int. Cl.
*A61F 7/00* (2006.01)
*A61F 7/02* (2006.01)
*A61F 7/10* (2006.01)

(52) U.S. Cl.
CPC ............ *A61F 7/0085* (2013.01); *A61F 7/007* (2013.01); *A61F 7/02* (2013.01); *A61F 7/10* (2013.01); *A61F 7/0097* (2013.01); *A61F 2007/0054* (2013.01); *A61F 2007/0056* (2013.01); *A61F 2007/0075* (2013.01); *A61F 2007/0203* (2013.01)

(58) Field of Classification Search
CPC combination set(s) only.
See application file for complete search history.

(56) References Cited

U.S. PATENT DOCUMENTS

| | | | |
|---|---|---|---|
| 4,259,961 A | 4/1981 | Hood et al. | |
| 4,298,006 A * | 11/1981 | Parks | A61F 7/123 128/898 |
| 4,691,762 A | 9/1987 | Elkins et al. | |
| 4,884,304 A | 12/1989 | Elkins et al. | |
| 5,097,828 A | 3/1992 | Deutsch | |
| 5,372,608 A * | 12/1994 | Johnson | A61F 7/10 607/104 |
| 5,470,353 A * | 11/1995 | Jensen | A61F 7/0097 607/104 |
| 5,683,439 A | 11/1997 | Jensen | |
| 5,871,526 A | 2/1999 | Gibbs et al. | |
| 5,895,418 A * | 4/1999 | Saringer | A61F 7/00 607/104 |
| 6,502,405 B1 | 1/2003 | Van Winkle | |
| 6,508,831 B1 | 1/2003 | Kushnir | |
| 6,551,347 B1 | 4/2003 | Elkins | |
| 7,211,104 B2 | 5/2007 | Edelman | |
| 9,283,109 B2 | 3/2016 | Guyuron et al. | |
| 2004/0249427 A1 | 12/2004 | Nabilsi | |

(Continued)

*Primary Examiner* — Joseph A Stoklosa
*Assistant Examiner* — Adam J Avigan
(74) *Attorney, Agent, or Firm* — Sunstein Kann Murphy & Timbers LLP

(57) ABSTRACT

A thermal therapy system includes at least one Peltier device having a heating side and a cooling side; a cold fluid reservoir adjacent the cooling side of the Peltier device, and a hot fluid reservoir adjacent the heating side of the Peltier device. A controllable cooling fluid pump in fluid communication with the cold fluid reservoir drives cooling fluid to an applicator pad, and an independently-controllable heating fluid pump in fluid communication with the hot fluid reservoir drives hot fluid to the applicator pad.

13 Claims, 19 Drawing Sheets

(56) References Cited

U.S. PATENT DOCUMENTS

| | | | |
|---|---|---|---|
| 2013/0138185 A1* | 5/2013 | Paxman | A61F 7/0085 607/104 |
| 2014/0222121 A1* | 8/2014 | Spence | A41D 13/005 607/104 |
| 2014/0257149 A1* | 9/2014 | Cotton | A61H 23/04 601/18 |
| 2018/0125702 A1* | 5/2018 | Roth | A61F 7/007 |
| 2018/0369015 A1 | 12/2018 | Glucksman et al. | |

* cited by examiner

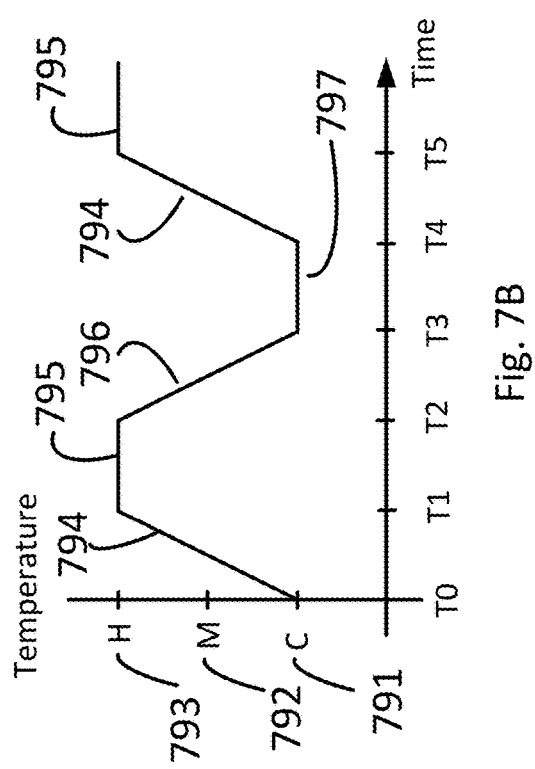

US 10,350,108 B1

HEATING/COOLING THERAPY SYSTEM

RELATED APPLICATIONS

This patent application claims priority from provisional U.S. patent application No. 62/694,281, filed Jul. 5, 2018, entitled "Heating/cooling Therapy System," and naming William J. Rittman III, Marsha Calise, and Steven Woolfson as inventors [practitioner's file 4394/1003], the disclosure of which is incorporated herein, in its entirety, by reference.

TECHNICAL FIELD

The present invention relates to therapy systems, and particularly to thermal therapy systems.

BACKGROUND ART

The uses of heating or cooling applicators to the skin for the treatment of injuries and pain have been used for a long time. These techniques are also known to improve the flexibility of tendons and ligaments, reduce muscle spasms and alleviate pain.

Heat therapy (also known as thermotherapy) is the heating of tissue by using various techniques, such as hot water bottles filled with hot water or cloth soaked in hot water, blankets or pads heated by internal electrical heating coils, or the application of ultrasound energy. Heat therapy leads to vasodilation, which in turn increases the blood flow in the affected tissues. The increased blood flow in the target area provides extra oxygen and other nutrients, thus accelerating the healing process. Additionally, the application of heat reduces muscle spasm and relaxes stretched muscles leading to pain relief. Heat or thermotherapy is generally used to treat chronic pain such as low back pain, spinal, neck pain, neuropathic pain, and other muscular spasms. Thermotherapy is generally applied in temperature range of 40-50° C.

Cold therapy (also known as cryotherapy), can be accomplished by using ice or a chemical gel. Cold therapy is typically used during the first one to two days after an injury, typically to get relief from bruises, bumps and sprains. Cold therapy soothes damaged tissues, causes vasoconstriction, which reduces blood circulation and thus numbs the nerves, decreasing inflammation, pain, and muscle spasm. Cold or cryotherapy is generally used to treat acute pain caused due to injuries such as runner's knee and freshly pulled muscle. Cryotherapy is generally applied in temperature range of 5-20° C.

Both therapies are effective for the treatment of edema and pain while being non-addictive and non-invasive.

Contrast therapy is another form of treatment which combines hot and cold therapy. It is performed through the alternate application of hot and cold packs on the skin of an injured area. It decreases pain, increases circulation, and speeds healing. Contrast therapy is used on sports injuries, chronic or repetitive injuries and injuries in the subacute stages of healing In terms of available products, the hot and cold therapy packs market can be divided into dry and moist hot and cold packs or compresses, gel packs, and electric hot/cold packs. There are many drawbacks to the products currently on the market that compromise their application:

Regarding heating, there are several techniques used to create a hot applicator. For example, some packs are designed to be microwaved, which suffer from drawbacks such as difficulty in controlling the temperature, can become too hot causing burns, and lose heat rapidly, necessitating the need to be reheated. Chemical packs are also commonly used, but they also have limitations based on lack of temperature control; they can leak and are therefore prone to cause chemical burns. The use of an electric heating coil in the pad is commonly used, but often does not have temperature control.

For cooling, ice packs that are kept in the freezer are most commonly used. They do not control temperature—the affected area can become too cold causing possible cold burns, they heat up rapidly, requiring the pack be frequently exchanged with a freshly cooled pack and placed back in the freezer to be refrozen. Chemical ice packs have the same drawbacks as the chemical heating packs. Pumped water from a container containing ice and water for cold therapy are bulky, require ice and water on hand. Further, the water can spill/leak, and there is no true temperature control.

To do combined heating and cooling therapy (contrast therapy) using these standard products would obviously require the purchase of two separate sets of products thus being expensive, requiring extra storage space and consuming a lot of time during application.

SUMMARY OF THE EMBODIMENTS

Described herein is an apparatus and a treating pad, being connected to each other via flexible conduits for enabling the pad to selectively cool or heat tissue. The apparatus includes at least one Peltier device attached to two reservoirs-one reservoir which is cooled and the other reservoir which is heated. Both reservoirs are filled with fluid such that using two pumps cold or hot water can be selectively pumped thru the conduit to the applicator pad in contact with the tissue. When using one Peltier device, this novel approach allows the device to cool and heat separate reservoirs simultaneously without the need of a second thermoelectric device or the need to reverse the current, which causes delays and expense. The cold reservoir at the cold side of the Peltier device should be encased in thermal insulation to prevent heat from being absorbed from the environment. The hot reservoir should have a heat sink disposed adjacent to it and a fan may be included on the heat sink. When using more than one Peltier device, including separate Peltier devices for heating and cooling, the cool side of the heating Peltier device, when in heating mode, can be used to cool the inside of the apparatus.

The apparatus also includes a control circuit including temperature and other controls, accessible to the user or operator for adjusting said temperatures and for selection of heating therapy, cooling therapy or contrast therapy. There is at least one temperature sensor that measures the temperature entering and/or leaving the applicator pad. The control circuit can maintain control over the temperature of the fluid in the applicator pad responsive to the at least one temperature sensor, by controlling the pumps, the Peltier device and/or the fan on the heat sink. Additionally, a thermal heater could be placed in the hot reservoir to provide additional heating.

The applicator pad is designed to conform to the shape of the tissue and is configured with at least one continuous liquid flow channel. The applicator pad also includes an insulation layer to ensure that no heat is lost to or absorbed by the environment on the non-treating side. The liquid flow channel can be created with a mold and two sheets of TPU (thermal polyurethane) or other flexible plastic or flexible tubing which is attached to the insulation layer. The applicator pad connects to the apparatus through an insulated flexible tube. There are two flexible conduits within the insulated tube, one serving as an intake fluid path for cooling or heating liquid to flow from the thermoelectric cooling apparatus to the pad and the other serving as a return fluid path. Preferably, self-sealing fluid connectors that allow the pad and/or conduit to be replaced or removed are used as opposed to permanent connection. Applicator pads can be supplied pre-loaded with fluid. By using the self-sealing fluid connectors, an applicator pad can be easily attached or detached without introducing air into the system. By using separate reservoirs to chill and to heat the tissue during use, the cooling and warming delays are greatly reduced no delay is needed to switch the thermoelectric device from cooling mode to warming mode.

The user interface is buttons on the apparatus and could also be controlled from a computer device or smart phone by Bluetooth or some other wireless means.

An illustrative embodiment of an electrical cooling/heating system includes at least one Peltier device having a heating side and a cooling side; a cold fluid reservoir adjacent the cooling side of the Peltier device; a hot fluid reservoir adjacent the heating side of the Peltier device; a cooling fluid pump in fluid communication with the cold fluid reservoir; a heating fluid pump in fluid communication with the hot fluid reservoir; a flexible pad having an application side, an insulation side and a continuous liquid flow channel, the channel having an inlet and an outlet; an intake fluid path having an end connected to the inlet and fed from each of the cooling fluid pump and the heating fluid pump; and a return fluid path having an end connected to the outlet and splitting to connect with each of the cold fluid reservoir and the hot fluid reservoir.

In some embodiments, the cold fluid reservoir includes a serpentine channel adjacent the cooling side of the Peltier device.

In some embodiments, the intake fluid path is unidirectional. To that end, some embodiments include, in each branch of the intake fluid path (one branch for the cooling fluid pump and one branch for the heating fluid pump), a one-way valve.

Some embodiments include a first temperature sensing device in the intake fluid path, and/or a second temperature sensing device in the return fluid path. Some such embodiments also include a controller responsive to the first temperature sensing device for controlling any of the cooling fluid pump, the heating fluid pump and/or the Peltier device.

Some embodiments include a heat sink adjacent the hot fluid reservoir and a fan operable for cooling the heat sink. In such embodiments, the controller may further respond to the first temperature sensing device by adjusting operation of the fan.

Some embodiments include a controller responsive to the first temperature sensing device and the second temperature sending device for controlling any of the cooling fluid pump, the heating fluid pump and/or the Peltier device.

In some embodiments, the flexible pad is detachable from the intake and return fluid paths. To that end, some embodiments include a first self-sealing valved connector comprised of a male connector part and a female connector part for connecting the intake fluid path to the inlet, and/or a second self-sealing valved connector comprised of a male connector part and a female connector part for connecting the return fluid path to the outlet.

Some embodiments further include an insulator pad, and a securable strap coupled to the insulator pad. The securable strap is and configured to secure the insulator pad against the flexible pad, and in some embodiments is also configures to secure the insulator pad and flexible pad to the user.

Illustrative embodiments of a flexible applicator pad for application of thermal therapy include an application side and an opposing side; a continuous liquid flow channel, the channel having an inlet and an outlet; a self-sealing inflow connector coupled to the inlet; a self-sealing outflow connector at the outlet; and a liquid sealed within the continuous liquid flow channel. Some such embodiments include an insulation layer on the opposing side.

Illustrative embodiments of an electrical cooling/heating system include a heating and cooling means for heating a first stream of liquid to produce a hot stream, and cooling a second stream of liquid to produce a cool stream; and a pump means for independently driving each of the hot stream and the cool stream, and for producing a single stream of liquid to an applicator pad, wherein the single stream of liquid is selected from one of the hot stream, the cool stream, or a mixture of the hot and cool stream.

In illustrative embodiments, the heating and cooling means includes a Peltier device having a heating side and a cooling side, a hot reservoir coupled to the heating side, and a cold reservoir coupled to the cooling side. In other embodiments, the heating and cooling means includes a heating Peltier device having a heating side; a hot reservoir coupled to the heating side of the Peltier device; a cooling Peltier device separate from the heating Peltier device, the cooling Peltier device having a cooling side; and a cold reservoir coupled to the cooling side.

In some embodiments, the pump means includes a hot pump in fluid communication with the heating and cooling means to drive the hot stream; and a cold pump in fluid communication with the heating and cooling means to drive the cool stream, the hot pump and the cold pump being independently controllable.

BRIEF DESCRIPTION OF THE DRAWINGS

The foregoing features of embodiments will be more readily understood by reference to the following detailed description, taken with reference to the accompanying drawings, in which:

FIG. 7B schematically illustrates a heating and cooling ramp.

DETAILED DESCRIPTION OF SPECIFIC EMBODIMENTS

Embodiments described herein provide to a user a compact and efficient personal heating and cooling system that is more reliable than previous heating and cooling systems. Preferred embodiments are controllable by the user to provide heating, or cooling, or alternate heating and cooling. To that end, illustrative embodiments produce a stream of hot water that is controllable for at least one of its temperature and flow rate, and a stream of cold water that is controllable (independently of the hot stream) for at least one of its temperature and flow rate, and provide heating, cooling, or alternate heating and cooling, by selectively forwarding to an applicator pad one of the hot stream or cold stream, or a mixture of the hot stream and cold stream.

Figures 1A, 1B:
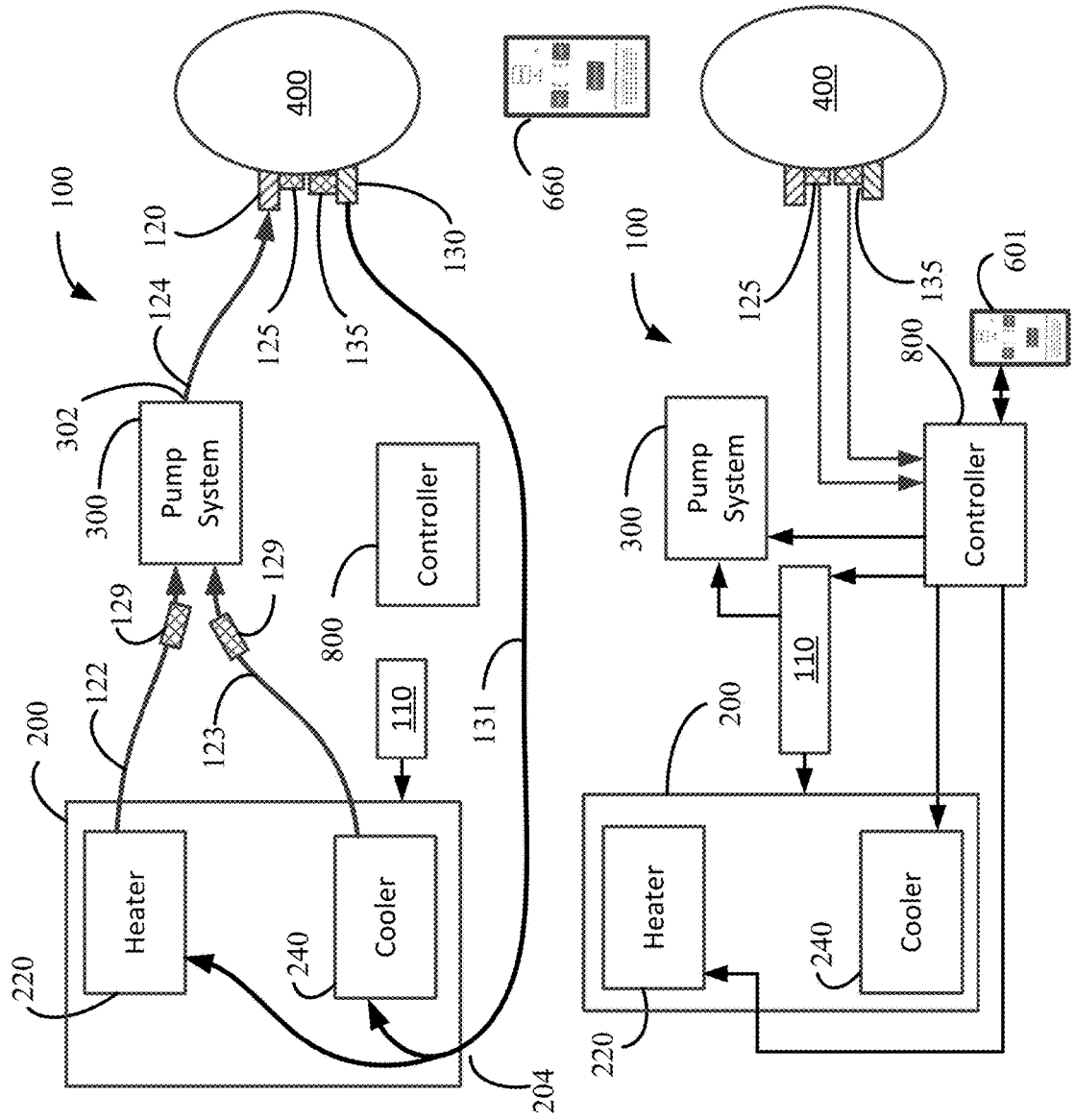
FIG. 1A and FIG. 1B schematically illustrate an embodiment of a heating/cooling system.

A first embodiment of a heating/cooling system 100 is schematically illustrated in FIG. 1A and FIG. 1B. The system 100 includes a fluid heating and cooling assembly 200 that, in operation, heats, cools, or alternately heats and cools a fluid, which fluid is then circulated through an applicator pad 400, described in more detail below. In preferred embodiments, the fluid is liquid, and is water, but in other embodiments the liquid may be a mix of water and other additives, or a liquid that is not water-based. Several embodiments of a heating and cooling assembly 200 are presented in the figures and described below.

The system 100 also includes a pump assembly 300 that includes at least one pump for driving the fluid from the heating and cooling assembly 200 through the applicator pad 400 and back to the heating and cooling assembly 200. Several embodiments of a pump assembly 300 are presented in the figures and described below. Unless otherwise specified, any embodiment of the heating and cooling assembly 200 will work with, and can be combined in a system 100 with, any embodiment of pump assembly 300.

FIG. 1A schematically illustrates fluid connections between the heating and cooling assembly 200, the pump assembly 300, and the applicator pad 400. In operation, a hot conduit 122 couples hot fluid produced by the heating and cooling assembly 200 to the pump assembly 300, and a cold conduit 123 couples cold fluid produced by the heating and cooling assembly 200 to the pump assembly 300. Hot fluid in the hot conduit 122 may be referred to as a hot stream, and cold fluid in the cold conduit may be referred to as a cold stream. As described in more detail, the pump assembly 300 controllably drives one of the hot stream or the cold stream, or a mixture of both hot stream and cold stream, to the applicator pad 400 through pad supply conduit 124.

In preferred embodiments, the pad supply conduit 124 is removably coupleable to the applicator pad 400 by a sealing connector 120. An illustrative embodiment of a sealing connector 120 is schematically illustrated in FIG. 4B and FIG. 4C. The sealing connector has a conduit connector 450 coupled to the pad supply conduit 124, and a pad connector 451 coupled to the input 412 of the raceway 410 in the applicator pad 400. In preferred embodiments, such that when the conduit connector 450 is mated to the pad connector 451, the sealing connector 120 allows fluid to pass from the pad supply conduit 124 to the raceway 410 of the applicator pad 400 without leaking fluid out or allowing air to enter the pad supply conduit 124 and/or raceway 410.

The system 100 also includes a return conduit 131 coupled to the applicator pad 400 and to the heating and cooling assembly 200. In illustrative embodiments, the return conduit is removably coupleable to an output 413 of the raceway 410, and to the heating and cooling assembly 200, and more specifically to both the heater 220 and cooler 240. In preferred embodiments, the pad supply conduit 124 is removably coupleable to the output 413 of the raceway 410 by a sealing connector 135. In preferred embodiments, at least one (and preferably each) of the connectors 120 and 130 is a valved connector, such that when the components of the connectors are coupled to one another, they form a fluid flow path that allows liquid to pass without leaking out and/or air leaking in, and when the components of the connectors are disconnected from one another, each component is seals such that no fluid leaks through such component.

In addition, the system 100 includes a power supply 110 in power communication with the heating and cooling assembly 200 and the pump assembly 300. The power supply 110, the heating and cooling assembly 200, and the pump assembly 300 are each in control communication with controller 800. In illustrative embodiments, the operation of the system 100 is controllable in one or more modes, under control of the controller 800. In preferred embodiments, the controller 800 is a BGM11S Blue Gecko System-in-Package Bluetooth Module available from Silicon labs, but in other embodiments the controller 800 may be a microcontroller such as the ATtiny88 available from Microchip Technology, Inc., to name but a few examples.

FIG. 1B schematically illustrates control and sensor connections within the system 100. For clarity, FIG. 1B omits the fluid conduits illustrated in FIG. 1A.

In some embodiments, it may be desirable to record the temperature of the fluid at one or more points of the raceway 410, and/or to control the operation of the heating and cooling system 100 based on one or more such temperature readings.

To that end, in preferred embodiments, the controller 800 is in sensing communication with one or both of supply temperature sensor 125 and return temperature sensor 135. The supply temperature sensor 125 is in thermal communication with the fluid supplied to the raceway 410 to measure the temperature of the incoming fluid, and the return sensor 135 is in thermal communication with the fluid at the output 413 of the raceway 410 to measure the temperature of the fluid leaving the applicator pad 400 after the fluid has circulated through the raceway 410.

In preferred embodiments, the controller 800 measures the temperature (Tin) of the fluid at the input 412 of the raceway 410 and the temperature (Tout) of the fluid at the output 413 of the raceway 410, and calculates the average of those temperatures as (Tin−Tout)/2. The controller 800 then uses that average temperature to control the operation of the heating and cooling system 100. Other embodiments may control the operation of the heating and cooling system based on only one of those temperatures (Tin or Tout), or based on the temperature (Tmid) of the fluid in the raceway 410 measured by a temperature sensor 136 disposed at a point of the fluid flow between the input 412 of the raceway 410 and the output 413 of the raceway 410.

The controller 800 is also in control communication with the power supply 110, the heating and cooling assembly 200, and the pump assembly 300. As described in more detail below, in various embodiments the controller 800 controls the power supply 110, the heating and cooling assembly 200, and the pump assembly 300 to operate the heating and cooling system 100 in one or more of several operational modes.

Figure 1C:
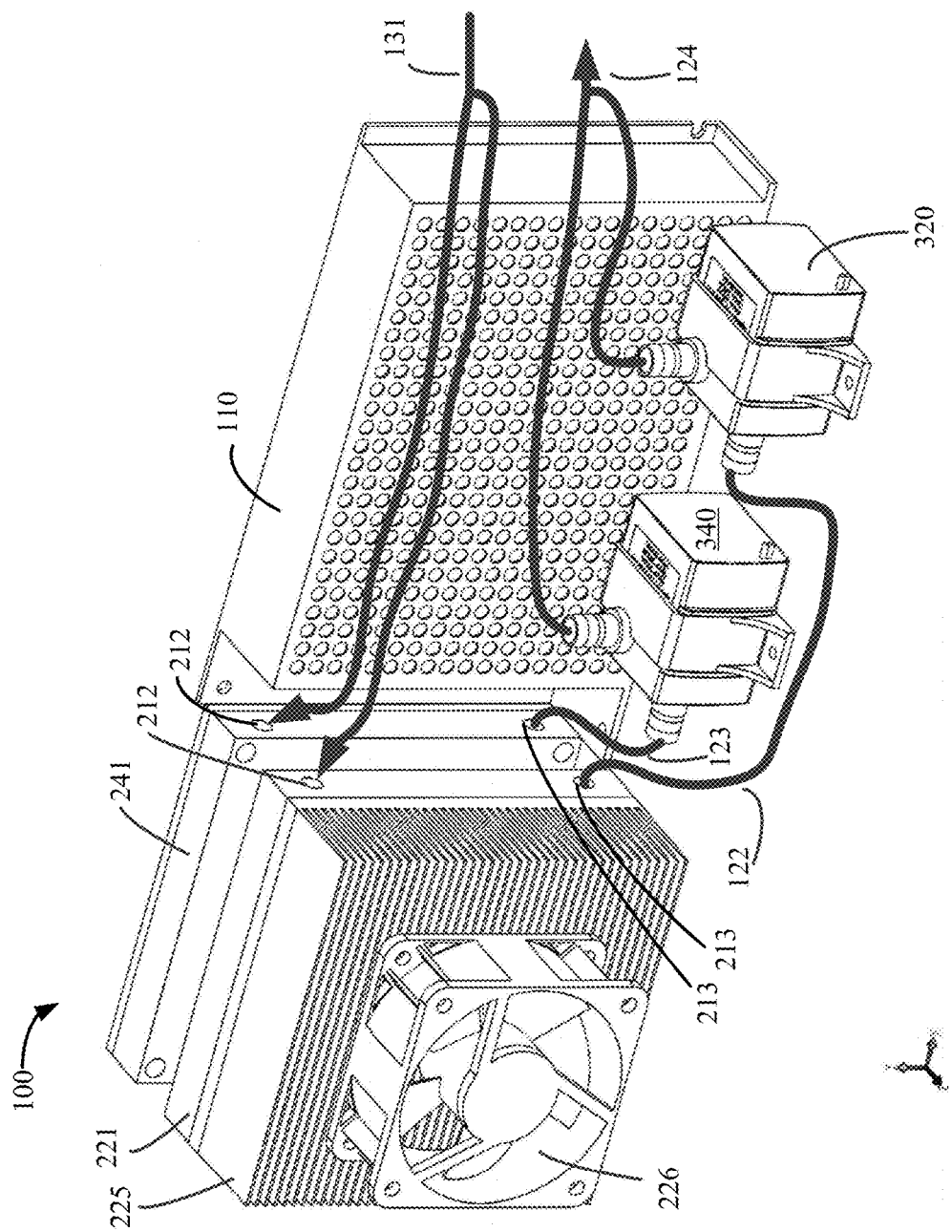
FIG. 1C and FIG. 1D schematically illustrate an embodiment of a heating/cooling system.
Figure 1D:
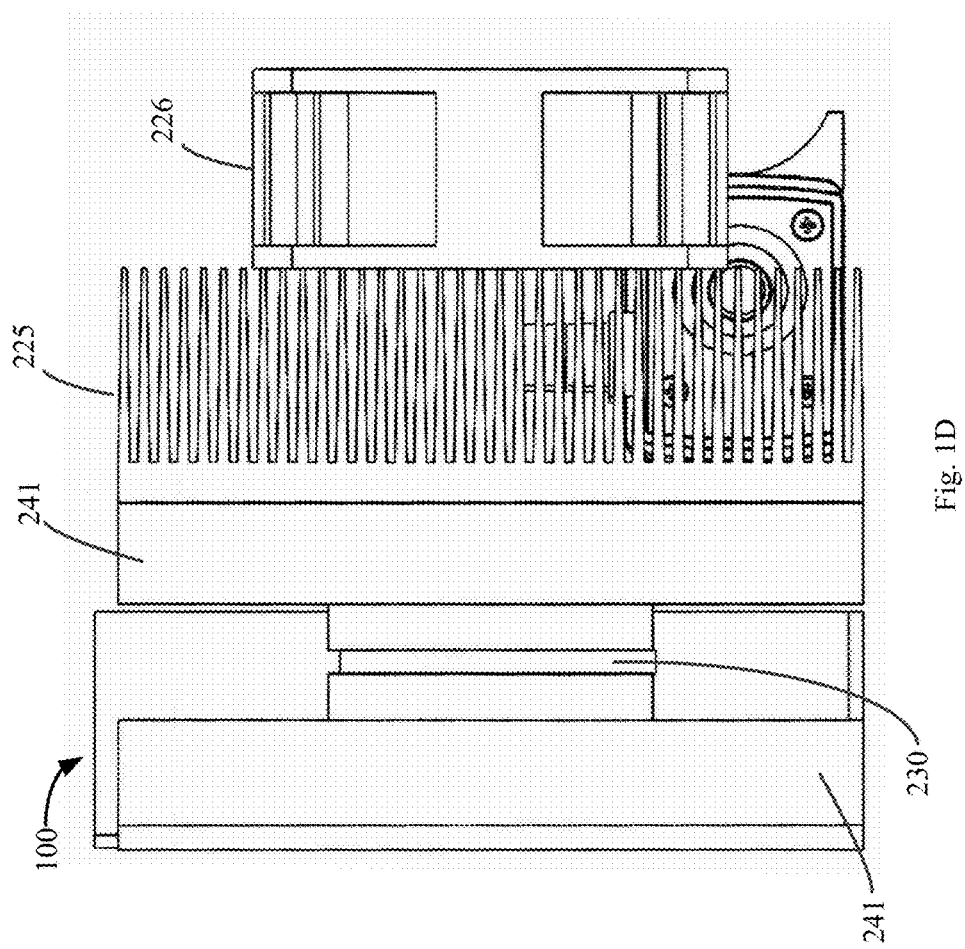

FIG. 1C and FIG. 1D schematically illustrate an embodiment of a heating/cooling system 100, which system includes a heating/cooling apparatus 200 for connection to an applicator pad 400. The heating/cooling apparatus 200 is designed to pump hot or cold fluid through an outlet port 302. Returning fluid is received in an inlet port 204. In order to provide hot and a cold fluid, a Peltier device 230, also known as a thermoelectric cooling unit ("TEC"), is sandwiched between a cold fluid reservoir 241 and a hot fluid reservoir 221. DC power is provided to the Peltier device 230 from a power supply 110. The power supply 110 may be sourced from an AC adaptor or from one or more batteries.

The hot fluid reservoir 221 is disposed next to the heating side of the Peltier device 230. To help keep the hot fluid from overheating, a heat sink 225 is attached to the hot fluid reservoir 221. In some embodiments, so as to provide additional cooling, a fan 226 is attached to the heat sink 225. Control over the rate of heating or cooling can be achieved by switching on or off the fan 226. Further control may be provided if the fan 226 is a variable speed fan that is electronically controlled, for example by controller 800. The cold fluid reservoir 241 is juxtaposed next to the cooling side of the Peltier device 230. On the external side of the cold fluid reservoir 241 an insulation layer 248 is provided to reduce environmental warming of the cooled fluid. In accordance with one embodiment of the reservoirs, they may be provided as a serpentine channel adjacent the Peltier device to promote heating or cooling as the case may be. FIG. 2B shows an example of such a serpentine channel 211 for use as the cold fluid reservoir. Such a channel could similarly be provided as the hot fluid reservoir. When a serpentine channel 211 is active through operation of the associated pump, fluid moves through the serpentine channel providing prolonged exposure to the heating or cooling effects of the Peltier device 230.

In order to move fluid in and out of the apparatus, a pump 320, 340, respectively, is provided for each reservoir. A heating fluid pump 320 is in fluid communication with an outlet port from the hot fluid reservoir 221. A cooling fluid pump 340 is in fluid communication with an outlet port from the cold fluid reservoir 241. An embodiment of a pump (e.g., 320, 330, 340) may be a centrifugal pump. As an alternative, a diaphragm pump may be used. Each of the pumps 320, 340, propels the respective fluid toward the outlet port 302. Since the fluid paths coincide at outlet port 302, a one-way valve 129, such as a check valve, may be disposed in each of the lines 122, 123 to prevent hot fluid from being pumped backwards into the cold fluid reservoir 241 and to prevent cold fluid from being pumped backwards into the hot fluid reservoir 221. A unidirectional flow of fluid is desirable. An insulated tubing 500 is provided with two conduits 124, 131. One conduit 124 connects to the outlet port 302 and the other 131 connects to the inlet port 204. At the distal end of each conduit, a self-sealing connector part (451 or 452) is attached.

Figure 1E:
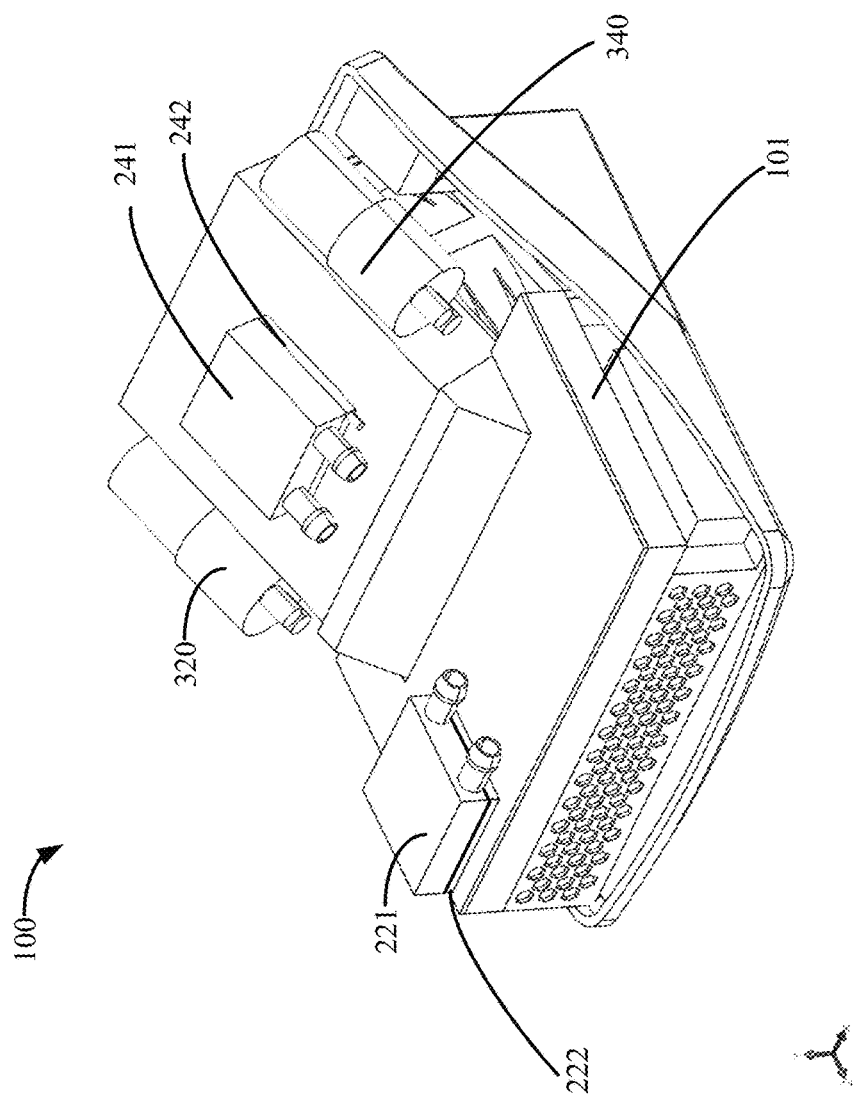
FIG. 1E, FIG. 1F and FIG. 1G schematically illustrate another embodiment of a heating/cooling system.
Figure 1F:
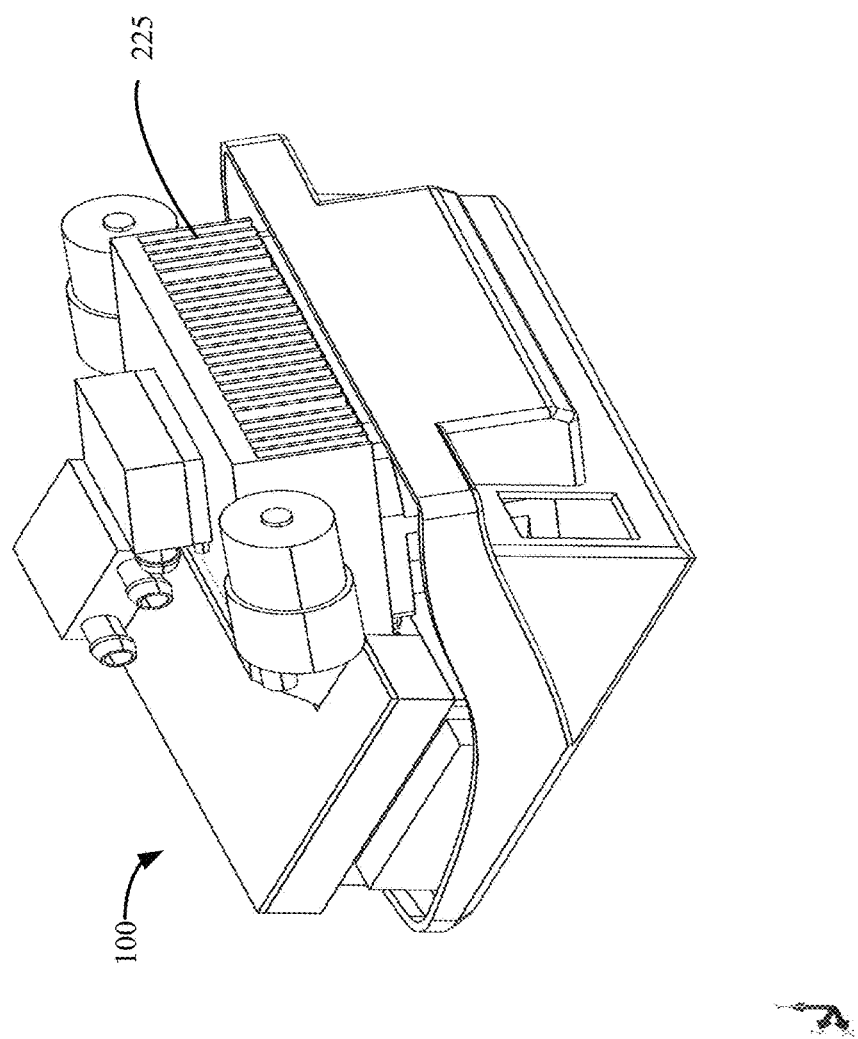
Figure 1G:
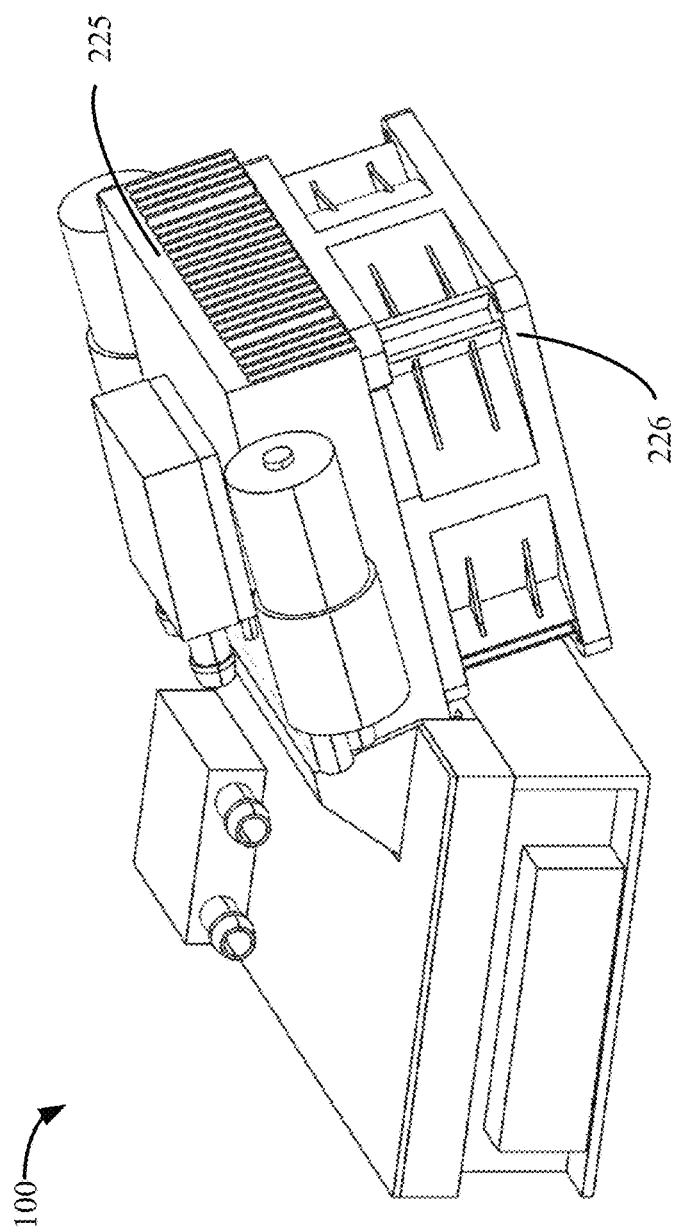

FIG. 1E, FIG. 1F, and FIG. 1G schematically illustrate another embodiment of a heating/cooling system 100. This embodiment includes an independently controllable heater 222 (which may be a Peltier device), and an independently controllable cooler 242, as described below in connection with FIG. 2A. This embodiment also includes an independently controllable hot pump 320, and an independently controllable cold pump 340, as described below in connection with FIG. 3A. Some embodiments include a heat sink 225 coupled to the cooler 242, as shown in FIG. 1F, and some embodiments include a fan 226 coupled to the heat sink, as shown in FIG. 1G.

Figure 1H:
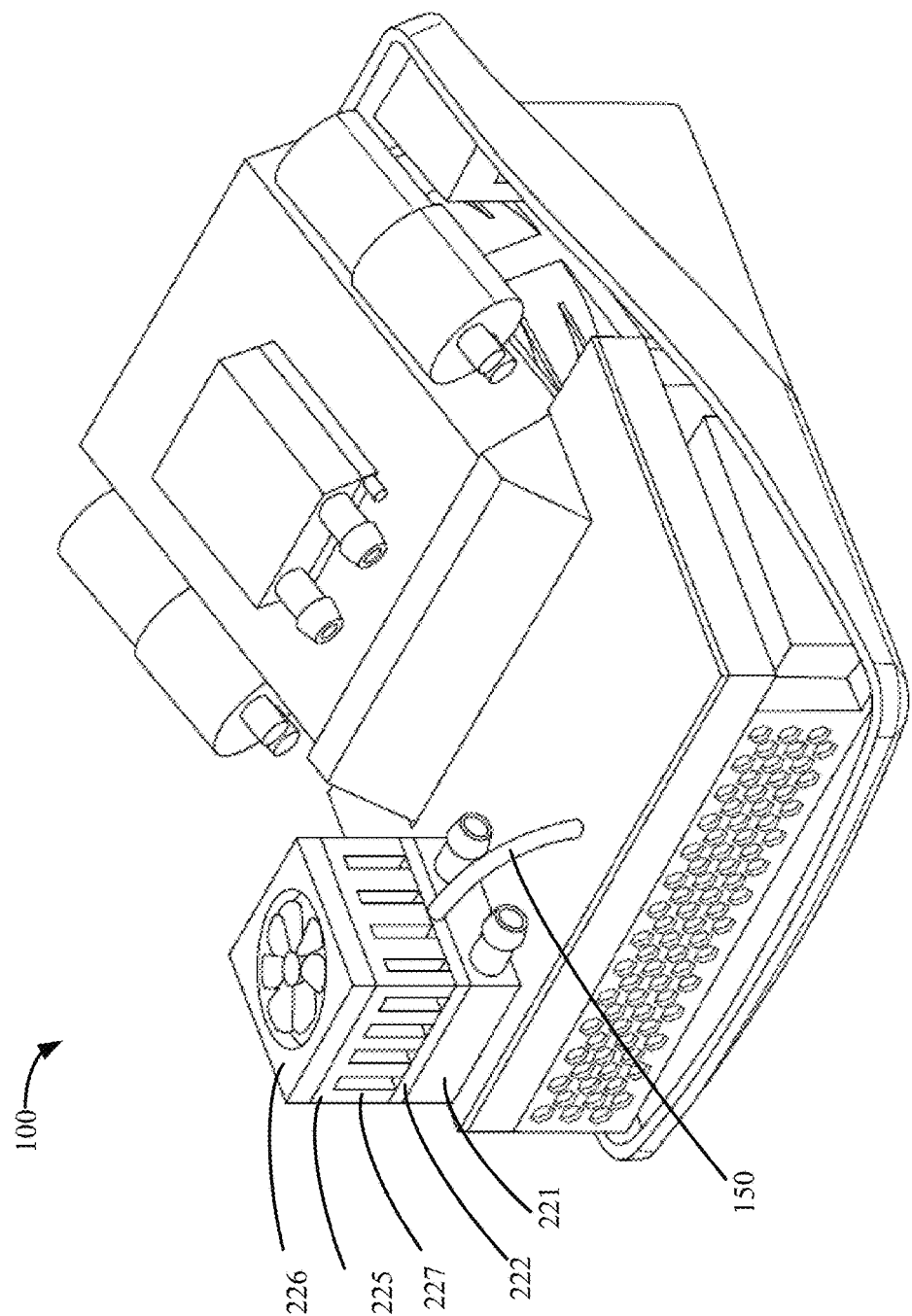
FIG. 1H schematically illustrates another embodiment of a heating/cooling system.

FIG. 1H schematically illustrates another embodiment of a heating/cooling system 100, in which a Peltier device 222 is disposed between the hot reservoir 221 and a heat sink 225 and fan 226, with the hot side of the Peltier device 222 adjacent to the hot reservoir 221, and the cold side of the Peltier device 222 facing away from the hot reservoir 221 and in thermal communication with the heat sink 225. In operation, the controller 800 controls the fan 226 (e.g., on, off, fan speed) to blow air over the heat sink 225 and into cool air conduit 150. The cool air conduit 150 is in fluid communication with the housing 101, so as to conduct cool air (i.e., air that has been cooled by the cold side of the Peltier device 222 and the heat sink 225) into an interior of the housing 101. The flow of such cool air cools circuitry and other components internal to the housing 101.

In some embodiments, the heater 222 may be disposed between the hot reservoir 221 and the housing 101 of the system 100. In embodiments that employ a Peltier device as the heater 222, the heating side of the Peltier device faces the hot reservoir 221, and the cold side of the Peltier device faces the housing 101. Such embodiments cool the housing 101, and any circuitry within the housing 101, by exposing the housing 101 to the cold side of the Peltier device.

Figure 2A:
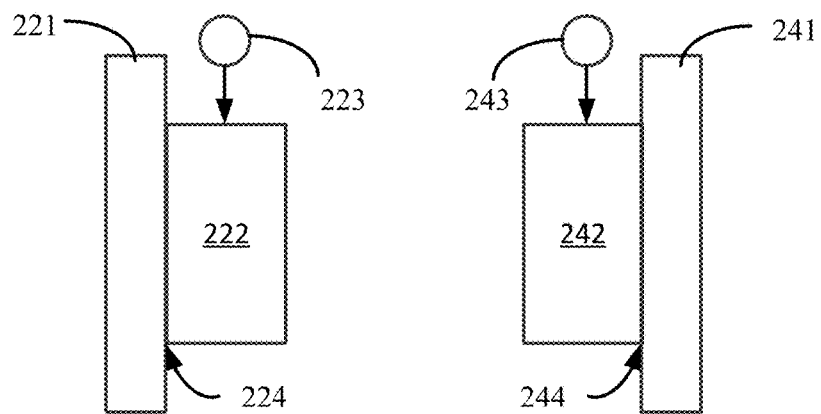
FIG. 2A schematically illustrates an embodiment of a fluid heater/cooler.
Figure 2B:
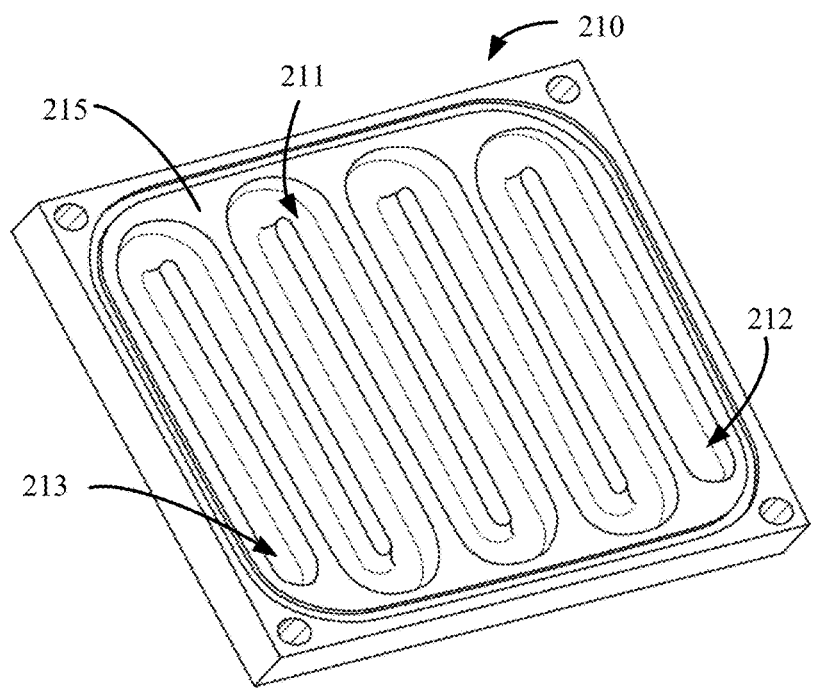
FIG. 2B schematically illustrates an embodiment of a reservoir.

FIG. 2A schematically illustrates an embodiment of a fluid heater and cooling assembly 200 having two thermal-electric devices, a first thermal electric device 222 disposed to heat all, or a portion of, fluid returning from the applicator pad 400, and a second thermal electric device 242 disposed to cool all, or a portion of, fluid returning from the applicator pad 400. In illustrative embodiments, the first thermal electric device 222 is a Peltier device, but in other embodiments the thermal electric device 222 may be only an electric-powered heat source.

In illustrative embodiments, each of the first thermal electric device 222 and the second thermal electric device 242 is a Peltier device. As known in the art, a Peltier device has two opposing sides. In operation, when electrical current passes through the Peltier device in a first direction, a first side of the Peltier device gets hot, and the opposite side gets cool. Moreover, when electrical current passes through the Peltier device in the opposite direction (a second direction), the first side of the Peltier device gets cool, and the opposite side gets hot. Consequently, a fluid may be heated by thermally coupling the fluid to a first side of a Peltier device an passing electrical current through the Peltier device in a first direction, and a fluid may be cooled by thermally coupling the fluid to a second side of a Peltier device an passing electrical current through the Peltier device in the second (opposite) direction.

Moreover, the fluid may be alternately heated and cooled by thermally coupling the fluid to a first side of a Peltier device and passing electrical current through the Peltier device in a first direction to heat, and reversing the electrical current to the second direction to cool. However, changing the direction of the electrical current is not preferred because the circuit required to controllably change the direction of the electrical current is more complex than a circuit that supplies current only in a single direction, and because changing the direction of current flow has deleterious effects on the performance of the Peltier device, including undesirably shortening the life span of the Peltier device. For that reason, some applications of Peltier devices avoid abrupt changes of electrical current direction, and instead have an intervening period of no current flow through the Peltier device prior to changing direction. Such an intervening period is undesirable in heating and cooling systems because it delays the change between heating and cooling modes.

To avoid such problems, the embodiment of FIG. 2A includes two Peltier devices, 222 and 242. A heating side 224 of a heating Peltier device 222 is thermally coupled to a heating reservoir 221. The heating side 224 is determined by the direction of electrical current flow through the Peltier device 222 from heater current source 223. The current source 223 is part of the power supply 110, and is in control communication with the controller 800. In preferred embodiments, the heater current source 223 is a unidirectional current source. The controller 800 can cause the current source 223 to drive electrical current through the Peltier device 222, modulate the quantity of electrical current flow through the Peltier device 222, and/or withhold electrical current from the Peltier device 222. In operation, fluid within, or flowing through, the heating reservoir 221 is heated by the heating Peltier device 222.

A cooling side 244 of a cooling Peltier device 242 is thermally coupled to a cooling reservoir 242. The cooling side 244 is determined by the direction of electrical current flow through the Peltier device 242 from cooler current source 243. The current source 243 is part of the power supply 110, and is in control communication with the controller 800. In preferred embodiments, the cooler current source 243 is a unidirectional current source. The controller 800 can cause the current source 243 to drive electrical current through the Peltier device 242, modulate the quantity of electrical current flow through the Peltier device 242, and/or withhold electrical current from the Peltier device 242. In operation, fluid within, or flowing through, the cooling reservoir 241 is cooled by the cooling Peltier device 242.

An embodiment of a reservoir 210, which may be a heating reservoir 221 or a cooling reservoir 241, is schematically illustrated in FIG. 2B. The reservoir 210 has a fluid flow channel 211 through a body 215. In preferred embodiments, the fluid flow channel 211 has a serpentine configuration, and the reservoir 210 may be referred to as a "manifold." In operation, fluid enters the fluid flow channel 211 through a reservoir inlet 212 and exits the fluid flow channel 211 through a reservoir outlet 213. In some embodiments, a hot reservoir 221 is the base 228 of a heat sink 225. Such a hot reservoir may be fabricated, for example, by machining the fluid flow channel 211 into the base 228 of the heat sink 225.

Figure 2C:
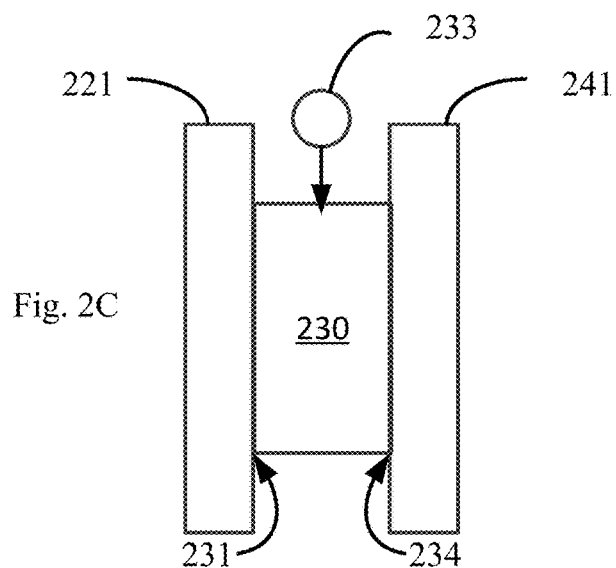
FIG. 2C schematically illustrates an alternate embodiment of a of a fluid heater/cooler.

FIG. 2C schematically illustrates an embodiment of a single-Peltier device heating and cooling assembly 200. In this embodiment, a single Peltier device 230 is shared by two reservoirs. The heating side 231 of the shared Peltier device 230 is thermally coupled to a heating reservoir 221, and the cooling side 234 of the shared Peltier device is thermally coupled to a cooling reservoir 241.

In operation, the shared Peltier device 230 heats fluid in, or flowing through the heating reservoir 221, and cools fluid flowing through the cooling reservoir 241. The operation of the shared Peltier device 230 is controlled by the controller 800. The controller 800 can cause the current source 233 to drive electrical current through the Peltier device 230, modulate the quantity of electrical current flow through the Peltier device 230, and/or withhold electrical current from the Peltier device 230.

As illustrated in FIG. 2C, the heating reservoir 221 is in thermal communication with the full heating side 231 of the shared Peltier device 230. In this way, all of the heat produced by the heating side 231 of the shared Peltier device 230 is thermally coupled to the heating reservoir 221.

Figure 2D:
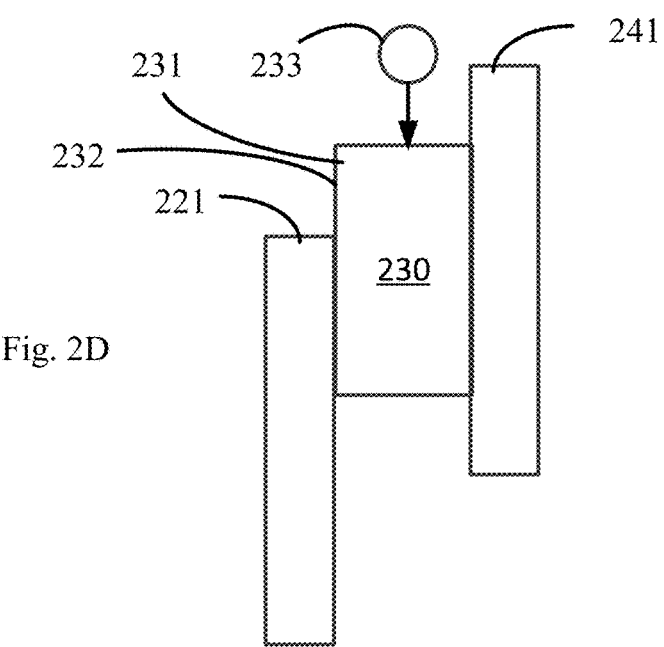
FIG. 2D schematically illustrates an alternate embodiment of a of a fluid heater/cooler.

In some embodiments, however, it may not be desirable to thermally couple all of the heat produced by the heating side 231 of the shared Peltier device 230 to the heating reservoir 221. For example, the shared Peltier device 230 may overheat the fluid if all of the heat produced by the shared Peltier device 230 is thermally coupled to the fluid. In some such embodiments, as schematically illustrated in FIG. 2D for example, the heating reservoir 221 is offset from the shared Peltier device 230, so that an exposed portion 232 of the heating side 231 of the shared Peltier device 230 is not in direct thermal contact with the heating reservoir 221. In such embodiments, heat at the exposed portion of the heating side 231 of the shared Peltier device 230 radiates into free space, or may be conductively coupled into a heat sink.

Figure 2E:
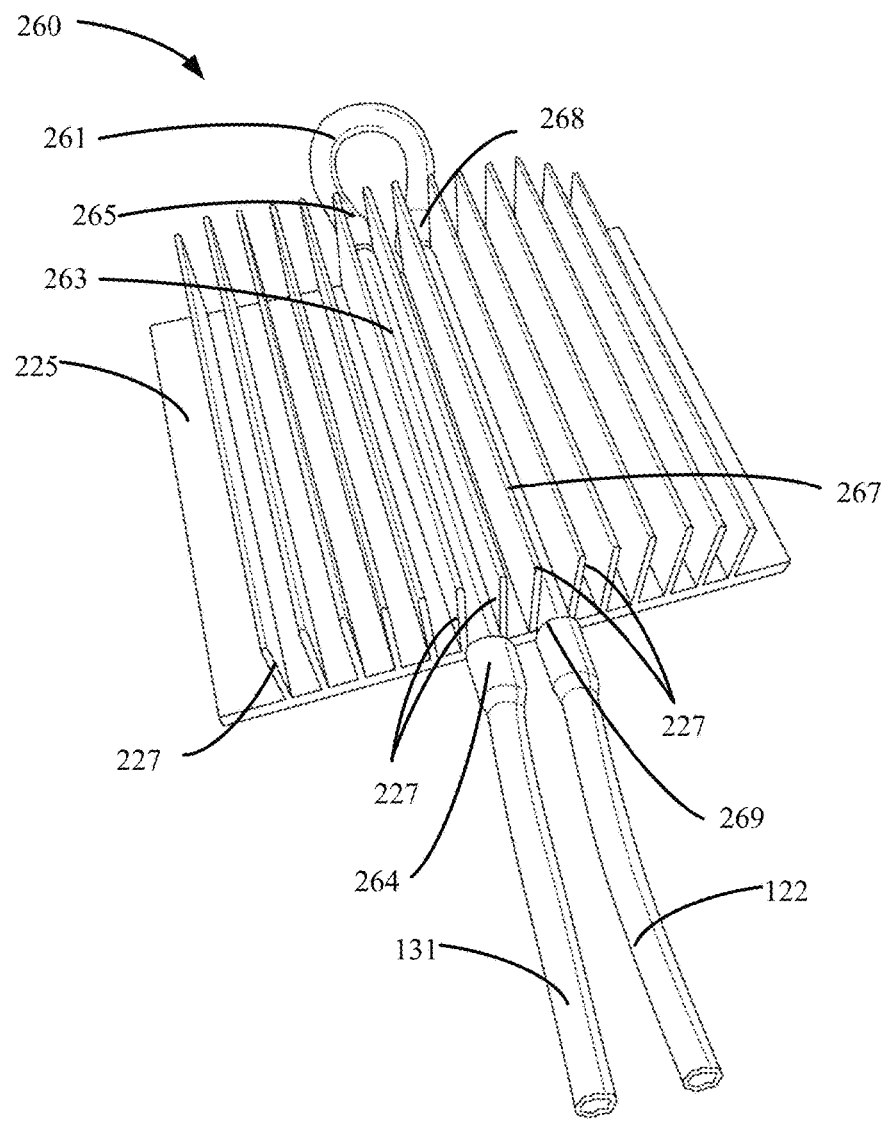
FIG. 2E schematically illustrates another embodiment of a fluid heater.

FIG. 2E schematically illustrates an alternate embodiment of a heat sink fluid heater 260 in which liquid in a heating conduit 261 is heated by exposure to a heat sink 225 that is coupled to a heat source 222. Such a heating conduit 261 is an embodiment of a hot reservoir 221. In the illustrative embodiment of FIG. 2E, the heating conduit 261 is disposed between fins 227 of a finned heat sink 225. In particular, in this illustrative embodiment, the heat sink 225 is a finned heat sink, and a segment 263 of the heating conduit 261 is disposed between one set of fins 227, and second segment 267 of the heating conduit 261 is disposed between a second set of fins 227. Each of the two segments 263 and 267 is preferably a copper tube. An input end 264 of the first segment 263 is coupled to return conduit 131 to receive fluid to be heated, and an output end 269 of the second segment 267 is coupled to hot supply conduit 122. The remaining ends 265 and 268 of each of the first and second segments 263 and 267, respectively, are coupled to each other by a loop 266 by which fluid passes from the first segment 263 to the second segment 267. In operation liquid from return conduit 131 is heated by heat from the heat sink 225 as it passes through the heating conduit 261, before exiting into the hot supply conduit 122.

Figure 2F:
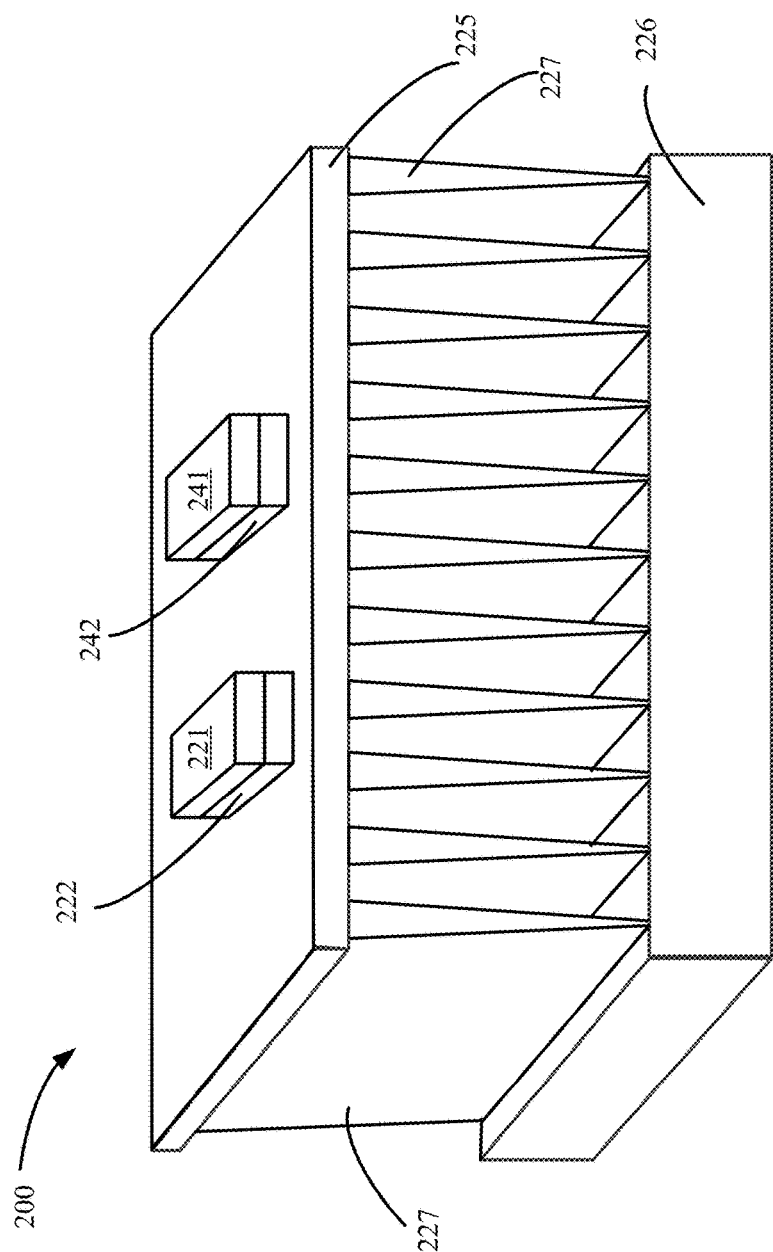
FIG. 2F schematically illustrates another embodiment of a fluid heater and fluid cooler system.

FIG. 2F schematically illustrates an alternate embodiment of a fluid heater and fluid cooler in which a heating Peltier device 222 is sandwiched between a hot reservoir 221 and a heat sink 225 such that the hot side of the Peltier device 222 is adjacent to the hot reservoir 221 and the cold side of the Peltier device is adjacent to the heat sink 225, and a cooling Peltier device 242 is sandwiched between a cold reservoir 241 and the heat sink 225 such that the cold side of the Peltier device 242 is adjacent to the cold reservoir 241 and the hot side of the Peltier device 242 is adjacent to the heat sink 225. In some embodiments, a fan 226 under control of the controller 800 blows air across the fins 227 of the heat sink 225. In these embodiments, heat generated by the cooling Peltier device 242 is conducted to the heat sink 225, and some of that heat is dissipated to the environment by the heat sink 225. Further, some heat generated by the cooling Peltier device 242 is conducted to the cold side of the heating Peltier device 222. In other words, when the heating Peltier device 222 is powered, the cold side of the heating Peltier device 222 cools the heat sink 225 directly, thereby absorbing some of the heat generated by the cooling Peltier device 242.

Figure 3A:
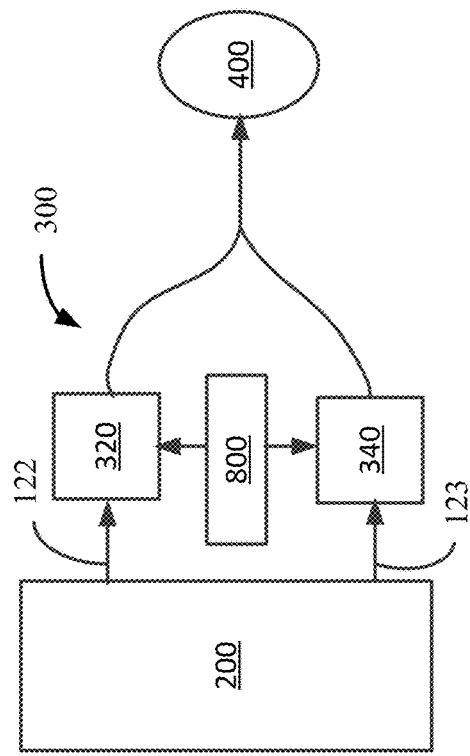
FIG. 3A schematically illustrates an embodiment of a pump system.
Figure 3B:
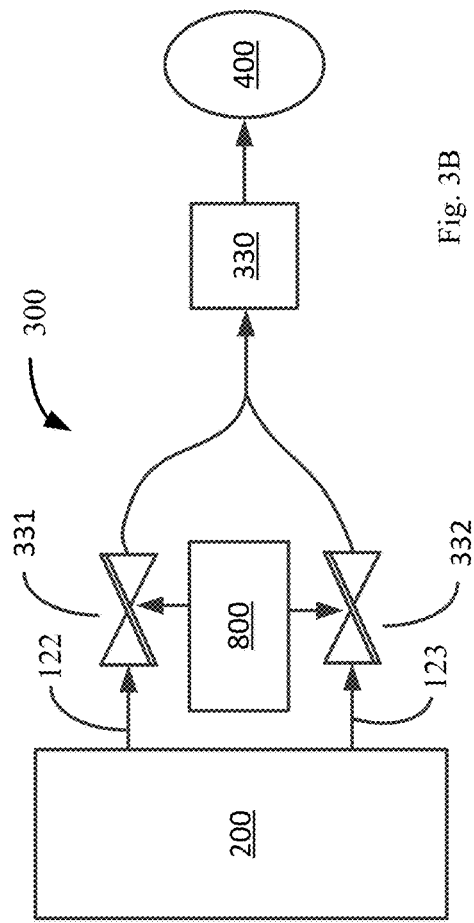
FIG. 3B schematically illustrates another embodiment of a pump system.

FIG. 3A and FIG. 3B schematically illustrates embodiments of a pump assembly 300, each of which produces an independently controllable stream of hot fluid and an independently controllable stream of cold fluid. In other words, the respective flow rates of the stream of hot fluid and the stream of cold fluid is controllable independently of one another.

FIG. 3A schematically illustrates an embodiment of a pump assembly 300 having two pumps, 320 340, each of which is independently under the control of controller 800.

The hot conduit 122 delivers to the hot pump 320 hot fluid from the heating and cooling assembly 200, and the cold conduit 123 deliver to the cold pump 340 cold fluid from the heating and cooling assembly 200. In operation, the controller 800 causes the hot pump 320 to drive hot fluid to the applicator pad 400 when the system 100 is in a heating mode, and causes the cold pump 340 drive cold fluid to the applicator pad 400 when the system 100 is in a cooling mode. In some embodiments, the pump assembly 300 may drive to the applicator pad 400 fluid having a temperature between the temperature of the hot fluid and the temperature of the cold fluid by causing each of the pumps 320 and 340 to drive fluid to the applicator pad 400. In such embodiments, hot fluid driven by hot pump 320 mixes, in the pad supply conduit 124 and/or in the pad 400, with cold fluid driven by the cold pump 340. Some embodiments gradually change the temperature of fluid supplied to the applicator pad 400 by gradually changing the amount of fluid driven by the hot pump 320 and the cold pump 340. For example, to increase the temperature of fluid supplied to the applicator pad 400, the quantity of fluid driven by the cold pump 340 may be decreased while the quantity of fluid driven by the hot pump 320 is increased. Similarly, to decrease the temperature of fluid supplied to the applicator pad 400, the quantity of fluid driven by the hot pump 320 may be decreased while the quantity of fluid driven by the cold pump 340 is increased.

FIG. 3B schematically illustrates another embodiment of a pump system having a single pump 330 and controllable valves 331, 332, all under control of the controller 800. In some embodiments, one or both of the controllable valves 331, 332 is a binary valve, in that the valve is controllable to be either completely open or completely closed. In other embodiments, one or both of the controllable valves 331, 332 is an adjustable valve, where the valve may be completely open, completely closed, or may be controlled to be adjusted to any point in a range between completely open and completely closed.

The hot conduit 122 delivers to the hot valve 331 hot fluid from the heating and cooling assembly 200, and the cold conduit 123 delivers to the cold valve 332 cold fluid from the heating and cooling assembly 200. In operation, the controller 800 causes the hot valve 331 to pass hot fluid to the shared pump 330 when the system 100 is in a heating mode, and causes the cold valve 332 to pass cold fluid to the shared pump 330 when the system 100 is in a cooling mode. In some embodiments, the pump assembly may drive to the applicator pad 400 fluid having a temperature between the temperature of the hot fluid and the temperature of the cold fluid by causing each of the valves 331 and 332 to pass hot and cold fluid, respectively, to the shared pump 330, whereby the shared pump 330 drives a mixture of hot and cold fluid to the applicator pad 400. Some embodiments gradually change the temperature of fluid supplied to the applicator pad 400 by gradually changing the amount of the hot fluid and cold fluid supplied to and driven by the shared pump 330. For example, to increase the temperature of fluid supplied to the applicator pad 400, the quantity of fluid passed by the cold valve 332 to the shared pump may be decreased while the quantity of fluid passed by the hot valve 331 to the shared pump 330 is increased. Similarly, to decrease the temperature of fluid supplied to the applicator pad 400, the quantity of fluid passed by the hot valve 331 320 may be decreased while the quantity of fluid passed by the cold valve 332 is increased.

Figure 4A:
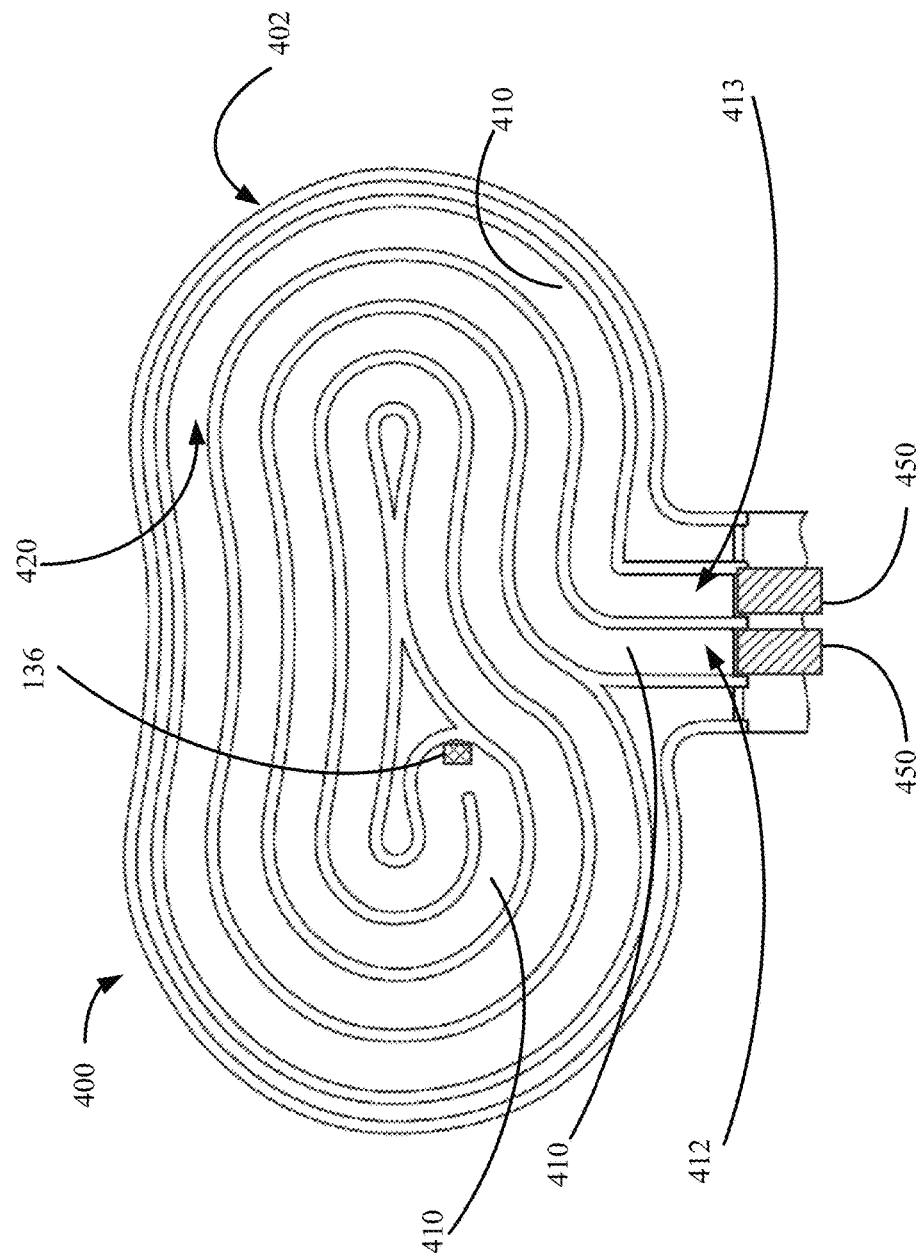
FIG. 4A schematically illustrates an embodiment of an applicator pad.
Figure 4B:
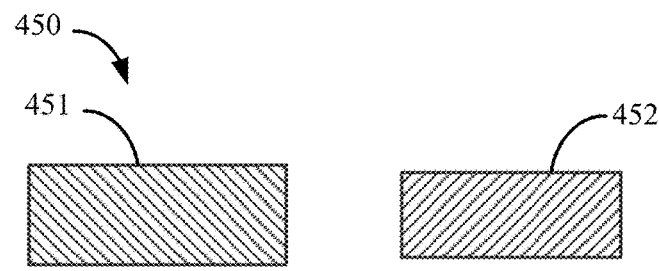
FIG. 4B schematically illustrates an embodiment of a self-sealing connector for use with the applicator pad of FIG. 4, in a detached condition.
Figure 4C:
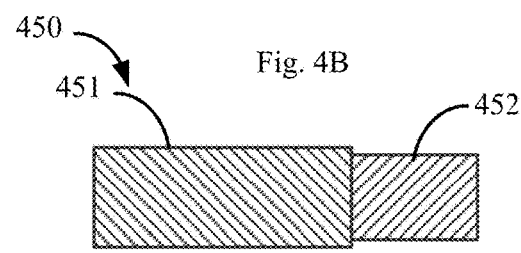
FIG. 4C schematically illustrates the embodiment of a self-sealing connector for use with the applicator pad of FIG. 4, in a coupled condition.
Figure 4D:
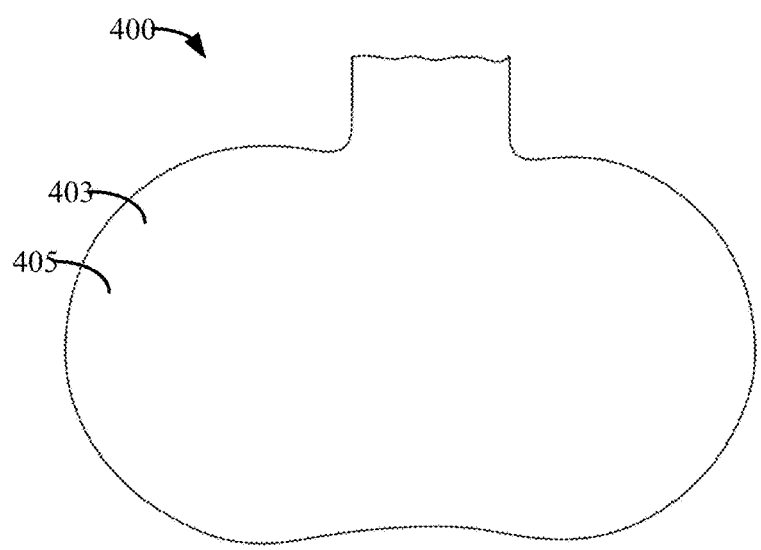
FIG. 4D schematically illustrates the opposites side of an applicator pad.

FIG. 4A schematically illustrates an embodiment of an applicator pad 400. The applicator pad 400 is flexible so that it may better conform to a body area being treated with the hot or cold therapy. A myriad of geometries of applicator pad 400 can be created to confirm to different body areas, and the disclosure herein is applicable to all such geometries. The figures in FIG. 4A, FIG. 4B, FIG. 4C and FIG. 4A are merely illustrative. A continuous liquid flow channel 410 (which may be referred to as a raceway) extends over almost the entire area of the pad 400. The channel 410 may be made by elongated tubing or by a use of a mold with two sheets of TPU (thermal polyurethane) or other suitable flexible plastic. A thermal insulation layer 405 extends over the non-treating side 403 of the pad 400, as schematically illustrated in FIG. 4D. The application side 402 of the pad 400 applies the heat or the cooling of the fluid in the flow channel 410 directly to the body area being treated. A self-sealing connector 451 is attached at each of the inlet end 412 and an outlet end 413 end of the liquid flow channel 410. The self-sealing connector parts 451, 452 of the applicator pad and the self-sealing connector part of the flexible tubing 500 are configured for making a mating connection. One of the mating connectors is in a male configuration and the other is a female configuration as shown in FIG. 4B and FIG. 4C. By including self-sealing connectors 450 in this way, the applicator pad 400 can be provided or sold with the channel 410 filled with liquid 420. When the conduits 124 and 131 of the flexible tubing 500 are similarly filled with liquid, connection can be made between the flexible tubing 500 and the applicator pad 400 without introducing troublesome air bubbles in the lines 124, 131 and channel 410, or allowing the fluid 420 to escape. Connection is therefore made simply without need for priming the continuous liquid flow channel 410.

FIG. 4B schematically illustrates an embodiment of a valved connector, which in this embodiments is a self-sealing connector 450 for use with the applicator pad of FIG. 4 and as the supply connector 120 and the return connector 130 in the apparatus of FIG. 1A and FIG. 1B in which a male mating connector 451 and a female mating connector 452 are schematically illustrated in a detached condition. In this condition, each of the male mating connector 451 and a female mating connector 452 is sealed, so that no fluid can pass.

FIG. 4C schematically illustrates the embodiment of a self-sealing connector 450 in which a male mating connector 451 and a female mating connector 452 are schematically illustrated in an attached condition. In this condition, the male mating connector 451 and female mating connector 452 form a passage through which fluid may flow without leaking out of a conduit or pad 400.

Figure 4E:
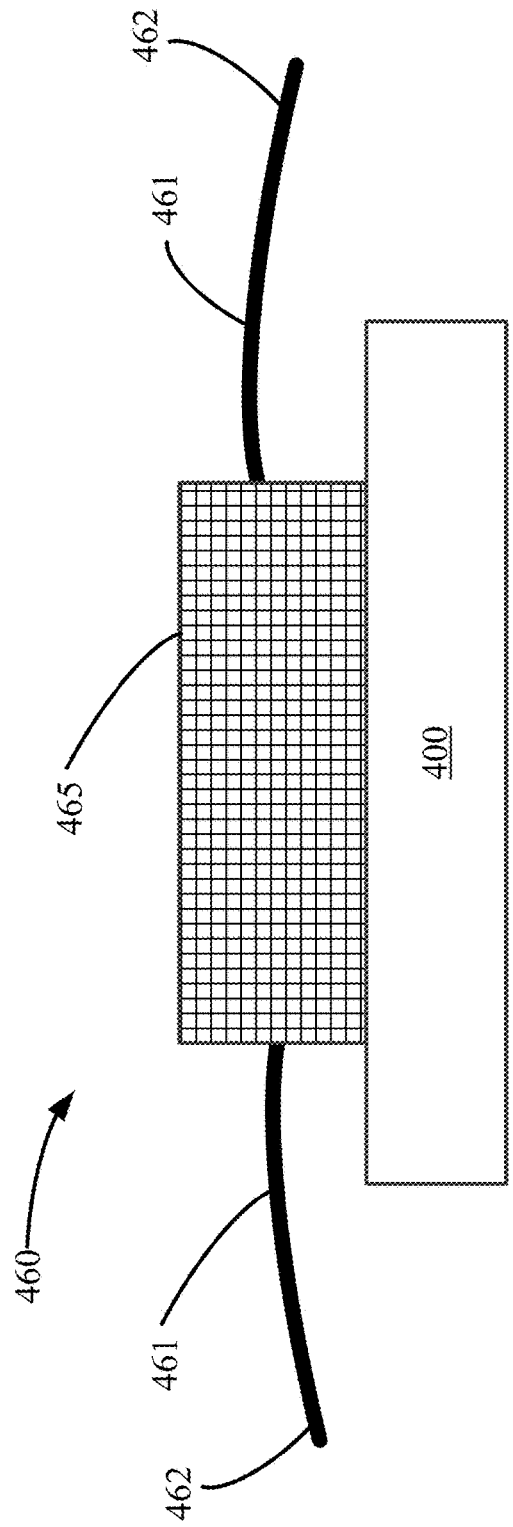
FIG. 4E schematically illustrates an embodiment of an insulator strap.

FIG. 4E schematically illustrates an embodiment of an insulator apparatus 460 that insulates the applicator pad to mitigate heat loss from fluid in the pad 400, or heat gain to fluid in the pad 400, in some embodiments, helps hold an applicator pad 400 to a user. The insulator apparatus 460 includes a strap 461 that may be secured around a part of the user, such a limb for example. In some embodiments, the opposing ends 462 of the strap 461 couple to one another to secure the strap in position. To that end, in some embodiments, the end 462 is a buckle or other fastening device. In other embodiments, the strap 461 is a hook and loop material (e.g., Velcro), and the ends of the strap 461 secure the insulator apparatus 460 by coupling to one another, or to an opposing hook and loop material on the pad 400, in ways known for hook and loop materials. In preferred embodiments, the insulator strap includes an insulator pad 465. In use, the insulator pad 465 is positioned adjacent to the applicator pad 400, as shown in FIG. 4E. More specifically, the insulator pad 465 is secured adjacent to the non-treating side 403 of the pad 400, to provide insulation against heating and/or cooling of fluid within the pad 400 from the environment or other heat source external to the pad 400. The insulator apparatus 460 is also removable. The insulator apparatus 460 may be described as including an insulator pad 465, and a securable strap 461 coupled to the insulator pad 465 and configured to secure the insulator pad 465 against the flexible applicator pad 400, for example when the applicator pad is secured to a user.

Figure 5A:
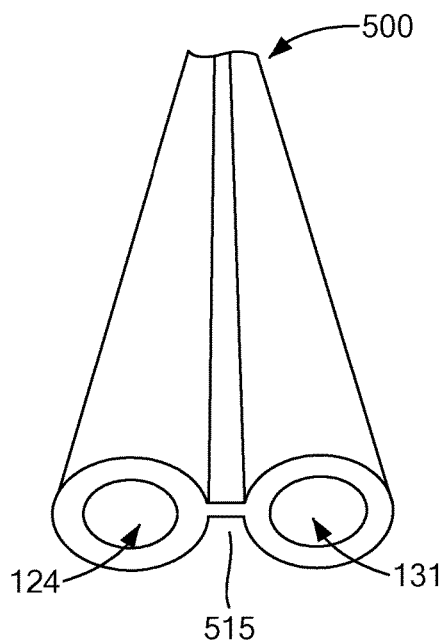
FIG. 5A and FIG. 5B schematically illustrate two embodiments of an insulated flexible tube for connecting the applicator pad of FIG. 4.

FIG. 5A schematically illustrates an embodiment of a flexible tube 500 for connecting the applicator pad 400 of FIG. 4 to the apparatus of FIG. 1A and FIG. 1B. The tube 500 includes a supply conduit 124 and a return conduit 131 coupled together by a joint 515.

Figure 5B:
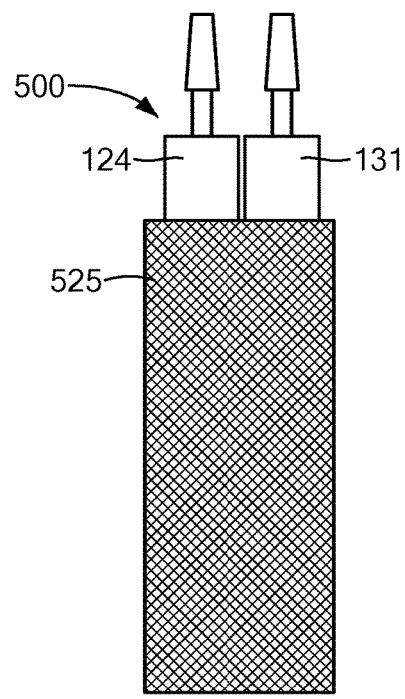

FIG. 5B schematically illustrates another embodiment of a flexible tube 500 for connecting the applicator pad 400 of FIG. 4 to the apparatus of FIG. 1A and FIG. 1B. The tube 500 includes a supply conduit 124 and a return conduit 131 coupled within a sheathing 525. In preferred embodiments, the sheathing 252 is a webbed sheathing.

In preferred embodiments of flexible tube 500, at least one and preferably both of the supply conduit 124 and a return conduit 131 is insulated to mitigate loss of heat from hot fluid, and warming of cold fluid, which loss of heat or warming may occur to or from the environment surrounding the flexible tube 500, and/or to or from the adjacent conduit 121 or 131, respectively.

Figure 6:
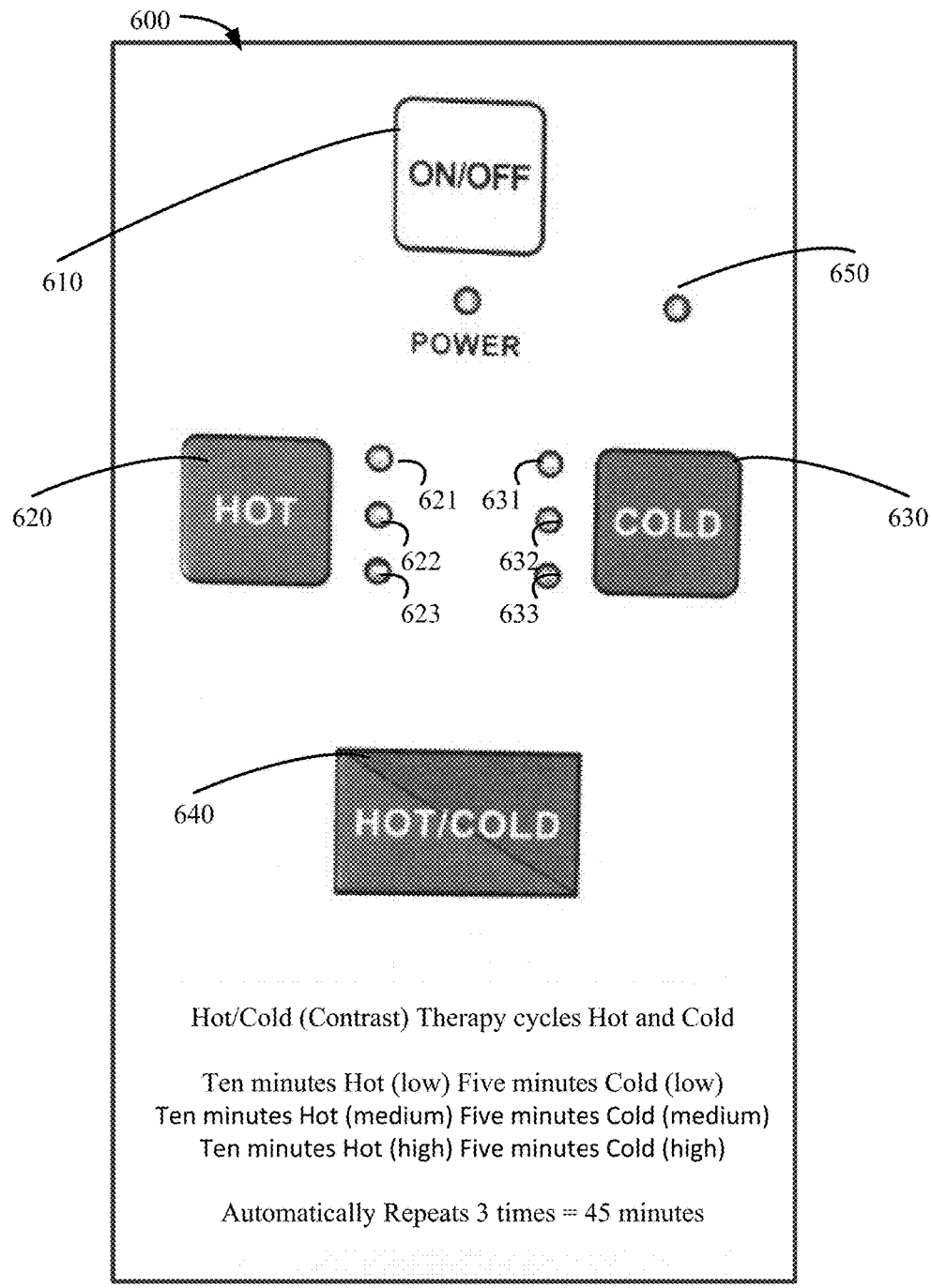
FIG. 6 is a plan view of a user interface panel for the apparatus.

FIG. 6 is a plan view of a user interface 600 for the apparatus 100 of FIG. 1A and FIG. 1B. In some embodiments, the user interface 600 is a physical panel 601 on the exterior of the apparatus 100. Alternatively, it may be a virtual control panel displayed on a screen 610 on the exterior of the apparatus 100. In some embodiments, the control panel 600 may be part of a remote control apparatus 660 (see FIG. 1B), which may be connected wirelessly or through a wire. A wireless connection may be through a protocol such as Bluetooth. The remote control 660 can be a dedicated controller or may be provided as an application (or "app") on a smartphone, a personal assistant or other computer device. Activation of a control may be manual or voice activated.

The user interface 600 has one or more control features, such as buttons or icons, by which the user may control the apparatus 100.

In preferred embodiments, the user interface 600 includes a power control feature 610 by the user may turn the apparatus 100 on and off.

Illustrative embodiments also include a heat control feature 620, by which the user can control the temperature of the hot fluid circulated to the pad 400. For example, illustrative embodiments allow the user to set the temperature of the hot fluid to any of several temperatures, such as low, medium, or high, by reputedly pressing or activating the heat control feature 620. The setting selected by the user may be indicated by the lighting of one or more of the lights 621, 622 and 623.

Illustrative embodiments also include a cold control feature 630, by which the user can control the temperature of the cooling fluid circulated to the pad 400. For example, illustrative embodiments allow the user to set the temperature of the cold fluid to any of several temperatures, such as low, medium, or high, by reputedly pressing or activating the heat control feature 630. The setting selected by the user may be indicated by the lighting of one or more of the lights 631, 632 and 633. In preferred embodiments, the control feature 630 allows a user to set the temperature of fluid supplied to the pad 400 to any temperature within the range of hot and cold temperatures capable of being produced by the apparatus 100. For example, in such embodiments, the control feature 630 may be a turnable knob, or a slider, to name but a few examples.

Preferred embodiments include a contrast therapy (or "Hot/Cold") control feature 640 by which a user may control the apparatus 100 to alternately apply hot therapy and cold therapy by switching between the supply of hot fluid and cold fluid.

Figure 7A:
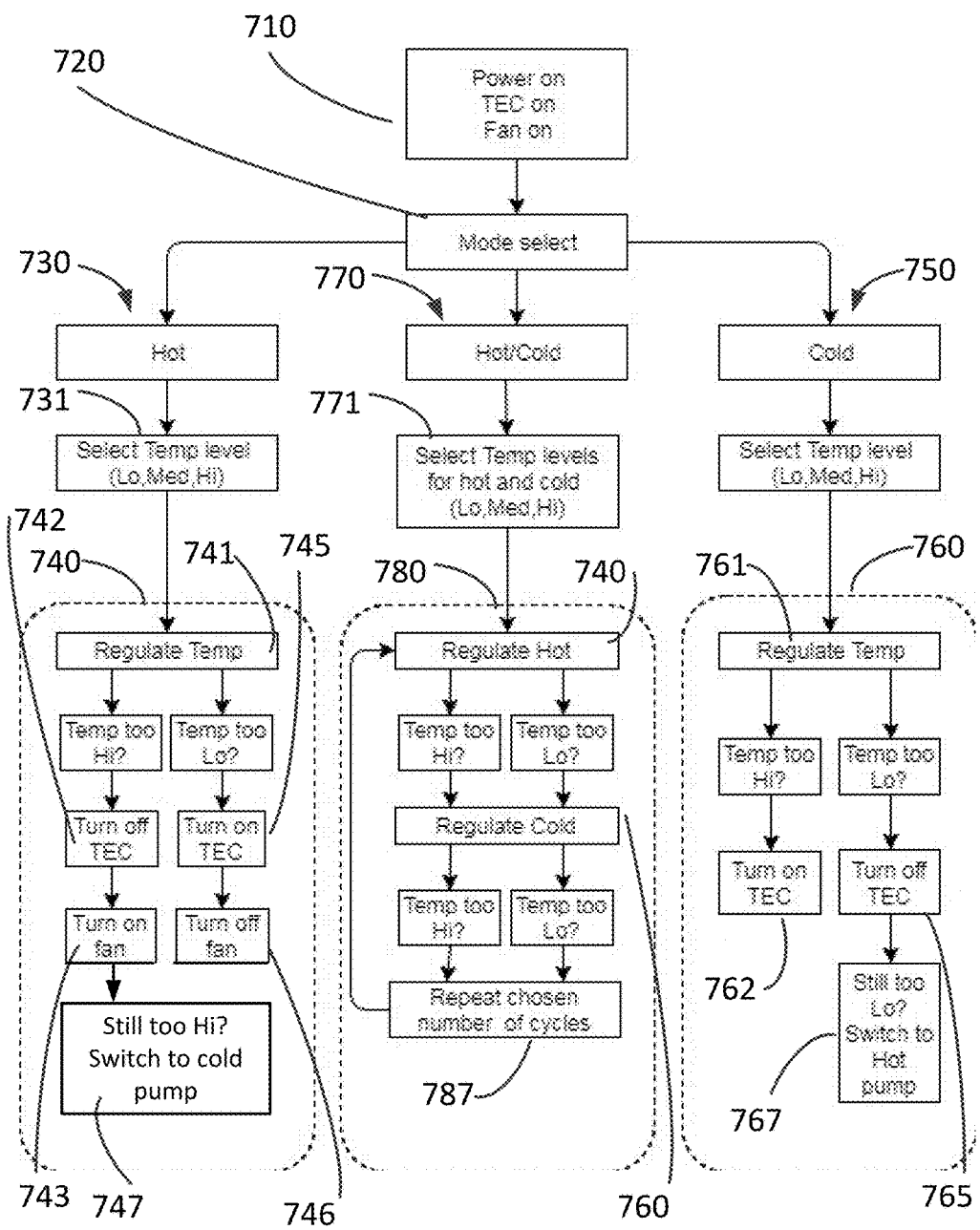
FIG. 7A is a flow chart of a method of operating a heating/cooling system.

FIG. 7A is a flow chart of embodiments of methods of operating a heating/cooling system 100. The control electronics 800 allows the user to select hot, cold or contrast therapies. A contrast therapy calls for alternating between cold and hot at designated intervals. By making hot and cold fluid reservoirs independently available (e.g., by providing independently-controllable pumps 320, 330, 340, or independently-controllable valves 331, 332, switching from one to the other can be accomplished with speed and ease. Moreover, temperature control can be maintained throughout the therapy quickly getting the temperature of fluid flowing through the applicator pad 400 to the desired level. In an illustrative embodiment, when cold fluid is called for the cold fluid pump 340 is switched on and the heating fluid pump 320 is switched off. Cold temperature is adjusted by turning on or off the Peltier device that cools the liquid (e.g., 242; 230). Cooling can also be facilitated by turning on or increasing the speed of fan 226. When the fluid in the cold reservoir 241 has been sufficiently cooled by the Peltier device for use, an indicator light 650 illuminates. The control electronics maintains the desired temperature by monitoring the first and second temperature sensors (125, 135). Thus, the temperature can be automatically adjusted to any level.

The method begins as step 710, at which the user powers-up the system 100, including the one or more Peltier devices (222, 242) and fan 226.

At step 720, the user selects an operating mode, for example a heating mode by activating the heat control feature 620, a cooling mode by activating the cold control feature 630, or the hot/cold mode by activating the hot/cold control feature 640.

When the user selects the heating mode, the method follows branch 730 of the flow chart. At step 731, the user selects the desired hot temperature, and the system 100 begins circulating hot fluid through the applicator pad 400. At step 741, the system measures the temperature of the fluid circulating through the applicator pad 400. In preferred embodiments, the system measures the temperature of the fluid both at the input 412 and outlet 413 of the applicator pad 400, and determines the temperature of the fluid as the average of those two measurements. The inventors have found that measuring the fluid temperature in that way provides a more reliable indication of the temperature of the fluid circulating within the applicator pad 400. Other embodiments, however, measure the temperature of the fluid either at the input 412 or output 413. The method assesses the measured fluid temperature to detect whether the fluid temperature exceeds the selected temperature (too high), or is below the selected temperature (too low).

When the temperature is too high, the method responds to cool the fluid. To that end, the method may reduce or stop the current flow supplied to the heater 221 heating the fluid (step 742), and/or may turn on the fan 226 (step 743). Some embodiments may also switch to the cooling mode 750 at step 747, at least until the fluid temperature returns to the selected temperature.

When the temperature is too low, the method responds to heat the fluid. To that end, the method may increase the current flow supplied to the heater 222 heating the fluid (step 745), and/or may turn off the fan 226 (step 746).

When the user selects the cooling mode, the method follows branch 750 of the flow chart. At step 751, the user selects the desired cold temperature, and the system 100 begins circulating hot water through the applicator pad 400. At step 761, the system 100 measures the temperature of the fluid circulating through the applicator pad 400. As described above, in preferred embodiments, the system measures the temperature of the fluid both at the input 412 and outlet 413 of the applicator pad 400, and determines the temperature of the fluid as the average of those two measurements, but other embodiments measure the fluid temperature at only a single point.

When the temperature is too high, the method responds to cool the fluid. To that end, the method may reduce or stop the current flow supplied to the Peltier device 242 that is cooling the fluid (step 762).

When the temperature is too low, the method responds to heat the fluid. To that end, the method may decrease the current flow supplied to the Peltier device 242 or turn off or reduce the speed of the fan 226, thereby cooling the fluid (step 765).

Some embodiments may also switch to the warming mode 730 at step 767, at least until the fluid temperature returns to the selected temperature.

When the user selects the hot/cold mode (or "contrast therapy" mode), the method follows branch 770 of the flow chart. In the hot/cold mode, the system 100 alternates between a heating mode described above, and the cooling mode described above. Preferred embodiments repeat that alternating cycle a set number of times, at step 787.

FIG. 7B schematically illustrates a heating and cooling ramp cycle. In hot/cold mode 770, the system alternates between heating mode 730 and cooling mode 750, as illustrated by temperature profile 790. In an illustrative embodiment, the system begins at a cold temperature indicated by point 791 on the temperature axis. In preferred embodiments, the system increases the temperature of fluid applied to the applicator pad 400 up through a moderate or embedment temperature 792, and then on to the hot temperature 793. The system 100 may cause this warming ramp 794 by changing the mix of hot fluid and cold fluid supplied by the pump assembly 300 to the applicator pad 400 to gradually include more hot fluid and less cold fluid.

The warming ramp 794 extends between time T0 and time T1. That time span is sufficiently long so that the change of temperature does not seem abrupt or uncomfortable for the user. For example, in illustrative embodiments, the time between T0 and T1 is one minute.

The cycle then holds the temperature at the hot temperature 793 for a heating period 795 between time T1 and time T3. In this illustrative embodiment, the heating period may be 5 minutes.

Next, the cycle decreases the temperature from the hot temperature 793, down through the moderate or embedment temperature 792, and on to the cold temperature 791. The system 100 may cause this cooling ramp 796 by changing the mix of hot fluid and cold fluid supplied by the pump assembly 300 to the applicator pad 400 to gradually include more cold fluid and less hot fluid.

The cooling ramp 796 extends between time T2 and time T3. That time span is sufficiently long so that the change of temperature does not seem abrupt or uncomfortable for the user. For example, in illustrative embodiments, the time between T2 and T3 is one minute.

The cycle then holds the temperature at the cold temperature 791 for a cooling period 797 between time T3 and time T4. In this illustrative embodiment, the cooling period may be 5 minutes.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed (prefaced with the letter "P" so as to avoid confusion with the actual claims presented below) includes:

P1: An electrical cooling/heating system including a heating and cooling assembly having a return fluid input; a hot fluid output and a cold fluid output; a pump assembly having a fluid interface disposed to receive hot fluid from the hot fluid output and cold fluid from the cold fluid output (in some embodiments, the fluid interface includes a hot fluid input in fluid communication with the hot fluid output, and a cold fluid input in fluid communication with the cold fluid output), and a pump output.

P2: The electrical cooling/heating system of P1, further including a flexible pad having an application side, an insulation side and a continuous liquid flow channel, the channel having an inlet configured to sealingly couple to the pump output, and an outlet configured to sealingly couple to the return fluid input.

P3: The electrical cooling/heating system of P1, further including a flexible pad having an application side, an insulation side and a continuous liquid flow channel, the channel having an inlet in fluid communication with the pump output, and an outlet configured in fluid communication with the return fluid input.

P4: The electrical cooling/heating system of P1, wherein the heating and cooling assembly includes:

a hot fluid reservoir having a hot return inlet coupled to the return fluid input, and a first output coupled to the hot fluid output;

a cold fluid reservoir separate from the hot fluid reservoir, the cold fluid reservoir having a cold return inlet coupled to the return fluid input, and a second output coupled to the cold fluid output;

a shared Peltier device having a heating side and a cooling side, the cooling side in thermal communication with the cold fluid reservoir, and the heating side in thermal communication with the hot fluid reservoir.

P5: The electrical cooling/heating system of P1, wherein the heating and cooling assembly includes:

a hot fluid reservoir having a hot return inlet coupled to the return fluid input, and a first output coupled to the hot fluid output;

a heating Peltier device having a heating side in thermal communication with the hot fluid reservoir;

a cold fluid reservoir separate from the hot fluid reservoir, the cold fluid reservoir having a cold return inlet coupled to the return fluid input, and a second output coupled to the cold fluid output;

a cooling Peltier device having a cooling side in thermal communication with the cold fluid reservoir.

P6: The electrical cooling/heating system of P1, wherein the pump assembly includes:

a controllable hot pump having the hot fluid input in fluid communication with the hot fluid output, a hot pump outlet; in fluid communication with the pump output; and a controllable cold pump having the cold fluid input in fluid communication with the cold fluid output, and a cold pump outlet in fluid communication with the pump output, wherein the cold pump is controllable independently of the hot pump, and wherein the pump output is fed from each of the cold pump and the hot pump.

P7: The electrical cooling/heating system of P1, wherein the pump assembly includes:

a shared pump having a pump input and a pump output;

a hot controllable valve fluidly coupled between the hot fluid output and the pump input; and a cold controllable valve fluidly coupled between the cold fluid output and the pump input;

wherein the hot controllable valve is controllable independently of the cold controllable valve, and wherein the shared pump drives both hot fluid supplied through the hot controllable valve, and cold fluid supplied through the cold fluid valve.

The following reference numbers are used in the foregoing description.

100: Heating and cooling system;
101: Housing;
110: Power supply;
120: Supply connector;
122: Hot supply conduit;
123: Cold supply conduit;
124: Pad supply conduit;
125: Supply temperature sensor;
129: One way valve or check valve;
130: Return connector;
131: Return conduit;
135: Return temperature sensor;
136: Intra-channel temperature sensor;
150: Cool air conduit;
200: Fluid Heater/Cooler system
204: Return inlet;
210: Reservoir;
211: Reservoir channel;
220: Fluid heater;
221: Hot reservoir;
222: Heater (for example, a Peltier device);
223: Heater current source;
225: Heat sink;
226: Fan;
227: Heat sink fin;
228: Heat sink base;
230: Shared heating and cooling device;
231: Heating side;
232: Exposed portion;
233: Shared current source;
234: Cooling side;
240: Fluid cooler;
241: Cold reservoir;
242: Cooler device;
243: Cooler current source;
248: Insulation layer;
260: Heat sink fluid heater;
261: Heating conduit;
263: First segment of heating conduit;
264: Input end of first segment;
265: Output end of first segment;
266: Fluid connector;
267: Second segment of heating conduit;
268: Input end of second segment;
269 Output end of second segment;
300: Pump system;
301: Pump assembly input interface;
302: Pump assembly output;
320: Hot pump;
330: Shared pump;
331: Hot valve;
332: Cold valve;
340: Cold pump;
400: Applicator pad;
402: Application side of applicator pad;
403: Non-treating side of applicator pad;
405: Thermal insulation layer;
410: Raceway;
412: Raceway input;
413: Raceway output;
420: Fluid (e.g., liquid) sealed within raceway;
451: First self-sealing, mateable connector;
452: Second self-sealing, mateable connector;
460: Insulator apparatus;
461: Strap;
462: End of strap;
465: Insulator pad;
500: Flexible tube;
515: Joint;
525: Sheathing;
600: User interface;
601: Control panel;
610: Power selector;
620: Heat mode selector;
621-623: Heat setting lights;
630: Cold mode selector;
631-633: Cold setting lights;
640: Hot/cold mode selector;
650: Temperature indicator light;
660: Remote control;

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. An electrical cooling/heating system comprising:
   at least one Peltier device having a heating side and a cooling side;
   a cooling serpentine channel adjacent the cooling side of the at least one Peltier device;
   a heating serpentine channel adjacent the heating side of the at least one Peltier device;
   a cooling fluid pump in fluid communication with the cooling serpentine channel;
   a heating fluid pump in fluid communication with the heating serpentine channel;
   a flexible pad having an application side, an insulation side and a continuous liquid flow channel, the channel having an inlet and an outlet;
   an intake fluid path having an end connected to the inlet and fed from each of the cooling fluid pump and the heating fluid pump; and
   a return fluid path having an end connected to the outlet and configured to remain open through a split connecting with each of the cooling serpentine channel and the heating serpentine channel, wherein operation of the cooling fluid pump is adapted to cause fluid to flow through the split along the path connected to the cooling serpentine channel and operation of the heating fluid pump is adapted to cause fluid to flow through the split along the path connected to the heating serpentine channel.

2. The electrical cooling/heating system of claim 1 further comprising a first temperature sensing device in the intake fluid path.

3. The electrical cooling/heating system of claim 2 further comprising a second temperature sensing device in the return fluid path.

4. The electrical cooling/heating system of claim 3, further comprising a controller responsive to the first temperature sensing device and the second temperature sending device for controlling any of the cooling fluid pump, the heating fluid pump and/or the at least one Peltier device.

5. The electrical cooling/heating system of claim 2 further comprising a controller responsive to the first temperature sensing device for controlling any of the cooling fluid pump, the heating fluid pump and/or the at least one Peltier device.

6. The electrical cooling/heating system of claim 5 further comprising a heat sink adjacent the heating serpentine channel and a fan operable for cooling the heat sink.

7. The electrical cooling/heating system of claim 6, wherein the controller may further respond to the first temperature sensing device by adjusting operation of the fan.

8. The electrical cooling/heating system of claim 1 wherein the intake fluid path is unidirectional.

9. The electrical cooling/heating system of claim 8, wherein each branch of the intake fluid path, one for the cooling fluid pump and one for the heating fluid pump, includes a one-way valve.

10. The electrical cooling/heating system of claim 1, wherein the flexible pad is detachable from the intake and return fluid paths.

11. The electrical cooling/heating system of claim 10, further comprising a first self-sealing valved connector comprised of a male connector part and a female connector part for connecting the intake fluid path to the inlet.

12. The electrical cooling/heating system of claim 11, further comprising a second self-sealing valved connector comprised of a male connector part and a female connector part for connecting the return fluid path to the outlet.

13. The electrical cooling/heating system of claim 1 further comprising an insulator pad, and a securable strap coupled to the insulator pad, and configured to secure the insulator pad against the flexible pad.

* * * * *

UNITED STATES PATENT AND TRADEMARK OFFICE
CERTIFICATE OF CORRECTION

Page 1 of 1

PATENT NO.         : 10,350,108 B1
APPLICATION NO.    : 16/116316
DATED              : July 16, 2019
INVENTOR(S)        : Rittman, III et al.

It is certified that error appears in the above-identified patent and that said Letters Patent is hereby corrected as shown below:

In the Claims

In Column 20, Line 3:
Replace "sending"
With --sensing--

Signed and Sealed this
First Day of October, 2019

Andrei Iancu
*Director of the United States Patent and Trademark Office*